United States Patent
Pollock et al.

(10) Patent No.: US 10,191,057 B2
(45) Date of Patent: Jan. 29, 2019

(54) METHODS OF DIAGNOSING, CLASSIFYING AND TREATING ENDOMETRIAL CANCER AND PRECANCER

(71) Applicants: THE TRANSLATIONAL GENOMICS RESEARCH INSTITUTE, Phoenix, AZ (US); Washington University, St. Louis, MO (US)

(72) Inventors: Pamela Pollock, Queensland (AU); Paul Goodfellow, Columbus, OH (US)

(73) Assignees: The Translational Genomics Research Institute, Phoenix, AZ (US); Washington University, St. Louis, MO (US)

( * ) Notice: Subject to any disclaimer, the term of this patent is extended or adjusted under 35 U.S.C. 154(b) by 0 days.

(21) Appl. No.: 15/088,099

(22) Filed: Mar. 31, 2016

(65) Prior Publication Data

US 2016/0209417 A1 Jul. 21, 2016

Related U.S. Application Data

(63) Continuation of application No. 13/973,614, filed on Aug. 22, 2013, now abandoned, which is a continuation-in-part of application No. 12/532,563, filed as application No. PCT/US2008/058065 on Mar. 24, 2008, now abandoned.

(60) Provisional application No. 60/982,093, filed on Oct. 23, 2007, provisional application No. 60/896,884, filed on Mar. 23, 2007.

(51) Int. Cl.
| | |
|---|---|
| *A61K 35/00* | (2006.01) |
| *G01N 33/574* | (2006.01) |
| *G01N 33/68* | (2006.01) |
| *A61K 31/519* | (2006.01) |
| *C12N 15/113* | (2010.01) |
| *C12Q 1/6886* | (2018.01) |

(52) U.S. Cl.
CPC ..... *G01N 33/57442* (2013.01); *A61K 31/519* (2013.01); *C12N 15/1138* (2013.01); *C12Q 1/6886* (2013.01); *G01N 33/6893* (2013.01); *A61K 35/00* (2013.01); *C12N 2310/14* (2013.01); *C12N 2310/531* (2013.01); *C12N 2320/30* (2013.01); *C12Q 2600/106* (2013.01); *C12Q 2600/156* (2013.01); *G01N 2333/71* (2013.01)

(58) Field of Classification Search
CPC .................................................... A61K 35/00
See application file for complete search history.

(56) References Cited

PUBLICATIONS

Kunii et al. (Cancer Res. Apr. 1, 2008; 68 (7): 2340-8).*
Byron et al. (Cancer Res. Sep. 1, 2008; 68 (17): 6902-7).*
Dutt et al. (Proc. Natl. Acad. Sci. USA. Jun. 24, 2008; 105 (25): 8713-7).*
St. Bernard et al. (Endocrinology. Mar. 2005; 146 (3): 1145-53).*
Mohammadi et al. (EMBO J. Oct. 15, 1998; 17 (20): 5896-904).*
Hernandez et al. (Clin. Cancer Res. Aug. 1, 2005; 11 (15): 5444-50).*
Pollock et al. (Oncogene. Nov. 1, 2007; 26 (50): 7158-62).*
Koziczak et al. (Oncogene. Apr. 29, 2004; 23 (20): 3501-8).*
Ohnishi et al. (Diagn. Mol. Pathol. Jun. 2006; 15 (2): 101-8).*
Kim et al. (Cancer Biol. Ther. 2016; 17 (1): 65-78).*

\* cited by examiner

*Primary Examiner* — Stephen L Rawlings
(74) *Attorney, Agent, or Firm* — Rodney J. Fuller; Booth Udall Fuller, PLC

(57) ABSTRACT

Diagnostic and therapeutic applications for endometrial cancer are described. The diagnostic and therapeutic applications are based on certain activation mutations in the FGFR2 gene and its expression products. The present invention is directed to nucleotide sequences, amino acid sequences, probes, and primers related to FGFR2 activation mutants and kits comprising these mutants to diagnosis and classify endometrial cancer in a subject.

6 Claims, 11 Drawing Sheets

Specification includes a Sequence Listing.

Figure 5A
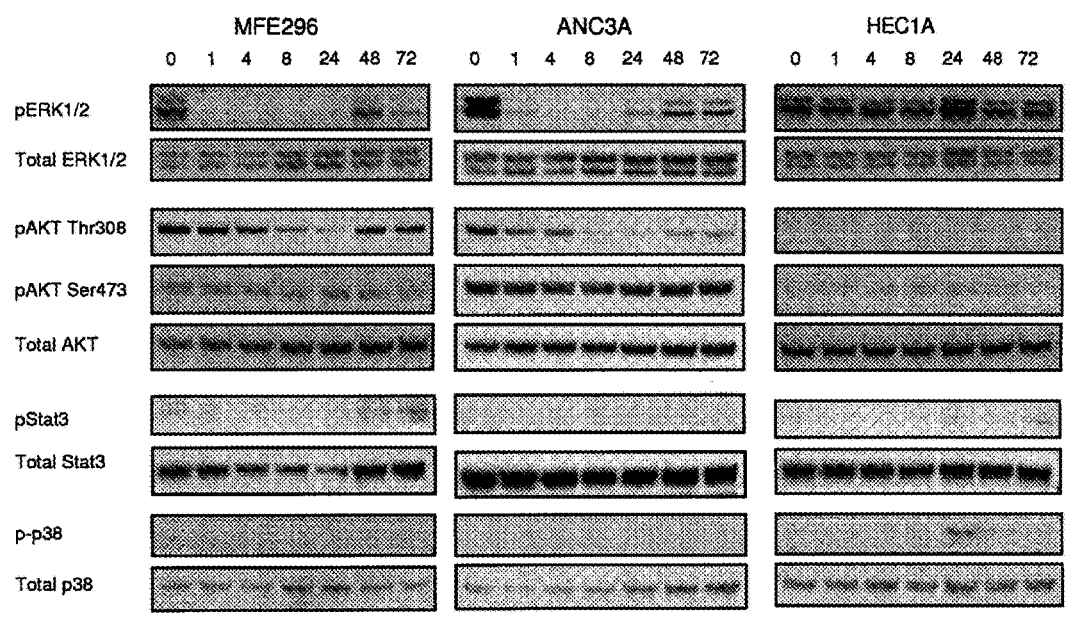
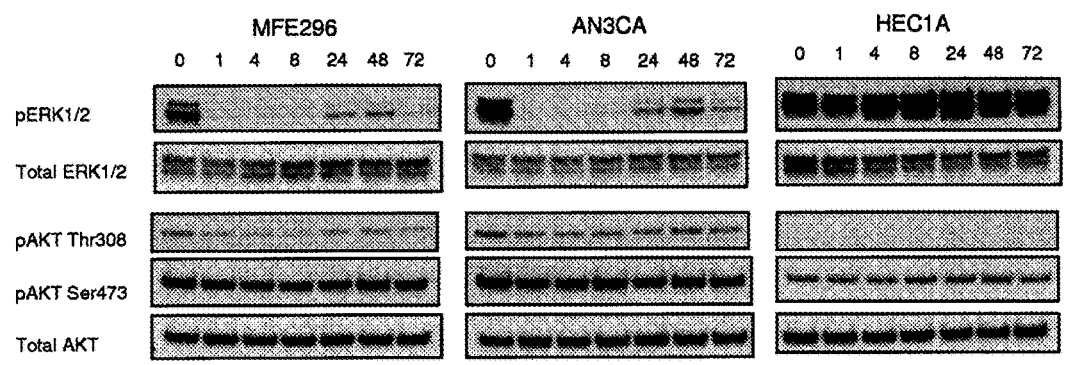
Figure 5B

SEQUENCE LISTING

<160> NUMBER OF SEQ ID NOS: 7

<210> SEQ ID NO 1
<211> LENGTH: 4647
<212> TYPE: DNA
<213> ORGANISM: Homo sapiens

<400> SEQUENCE: 1

```
ggcggcggct ggaggagagc gcggtggaga gccgagcggg cgggcggcgg gtgcggagcg      60
ggcgagggag cgcgcgcggc cgccacaaag ctcgggcgcc gcggggctgc atgcggcgta     120
cctggcccgg cgcggcgact gctctccggg ctggcggggg ccggccgcga gccccggggg     180
ccccgaggcc gcagcttgcc tgcgcgctct gagccttcgc aactcgcgag caaagtttgg     240
tggaggcaac gccaagcctg agtcctttct tcctctcgtt ccccaaatcc gagggcagcc     300
cgcgggcgtc atgcccgcgc tcctccgcag cctggggtac gcgtgaagcc cgggaggctt     360
ggcgccggcg aagacccaag gaccactctt ctgcgtttgg agttgctccc cgcaaccccg     420
ggctcgtcgc tttctccatc ccgacccacg cggggcgcgg ggacaacaca ggtcgcggag     480
gagcgttgcc attcaagtga ctgcagcagc agcggcagcg cctcggttcc tgagcccacc     540
gcaggctgaa ggcattgcgc gtagtccatg cccgtagagg aagtgtgcag atgggattaa     600
cgtccacatg gagatatgga agaggaccgg ggattggtac cgtaaccatg gtcagctggg     660
```

```
gtcgtttcat ctgcctggtc gtggtcacca tggcaacctt gtccctggcc cggccctcct      720
tcagtttagt tgaggatacc acattagagc cagaagagcc accaaccaaa taccaaatct      780
ctcaaccaga agtgtacgtg gctgcgccag gggagtcgct agaggtgcgc tgcctgttga      840
aagatgccgc cgtgatcagt tggactaagg atgggggtgca cttggggccc aacaatagga     900
cagtgcttat tggggagtac ttgcagataa agggcgccac gcctagagac tccggcctct      960
atgcttgtac tgccagtagg actgtagaca gtgaaacttg gtacttcatg gtgaatgtca     1020
cagatgccat ctcatccgga gatgatgagg atgacaccga tggtgcggaa gattttgtca     1080
gtgagaacag taacaacaag agagcaccat actggaccaa cacagaaaag atggaaaagc     1140
ggctccatgc tgtgcctgcg gccaacactg tcaagtttcg ctgcccagcc ggggggaacc     1200
caatgccaac catgcggtgg ctgaaaaacg gaaggagtt taagcaggag catcgcattg      1260
gaggctacaa ggtacgaaac cagcactgga gcctcattat ggaaagtgtg gtcccatctg     1320
acaagggaaa ttatacctgt gtagtggaga tgaatacgg gtccatcaat cacacgtacc      1380
acctggatgt tgtggagcga tcgcctcacc ggcccatcct ccaagccgga ctgccggcaa     1440
atgcctccac agtggtcgga ggagacgtag agtttgtctg caaggtttac agtgatgccc     1500
agccccacat ccagtggatc aagcacgtgg aaaagaacgg cagtaaatac gggcccgacg     1560
ggctgcccta cctcaaggtt ctcaagcact cggggataaa tagttccaat gcagaagtgc     1620
tggctctgtt caatgtgacc gaggcggatg ctggggaata tatatgtaag gtctccaatt     1680
atatagggca ggccaaccag tctgcctggc tcactgtcct gccaaaacag caagcgcctg     1740
gaagagaaaa ggagattaca gcttccccag actacctgga gatagccatt tactgcatag     1800
gggtcttctt aatcgcctgt atggtggtaa cagtcatcct gtgccgaatg aagaacacga     1860
ccaagaagcc agacttcagc agccagccgg ctgtgcacaa gctgaccaaa cgtatccccc     1920
tgcggagaca ggtaacagtt tcggctgagt ccagctcctc catgaactcc aacaccccgc     1980
tggtgaggat aacaacacgc ctctcttcaa cggcagacac ccccatgctg gcagggggtct    2040 ccgagtatga acttccagag gacccaaaat gggagtttcc aagagataag ctgacactgg     2100
gcaagcccct gggagaaggt tgcttttggc aagtggtcat ggcggaagca gtgggaattg     2160
acaaagacaa gcccaaggag gcggtcaccg tggccgtgaa gatgttgaaa gatgatgcca     2220
cagagaaaga cctttctgat ctggtgtcag agatggagat gatgaagatg attgggaaac     2280
acaagaatat cataaatctt cttggagcct gcacacagga tgggcctctc tatgtcatag     2340
ttgagtatgc ctctaaaggc aacctccgag aatacctccg agcccggagg ccacccggga     2400
tggagtactc ctatgacatt aaccgtgttc ctgaggagca gatgaccttc aaggacttgg     2460
tgtcatgcac ctaccagctg ccagaggca tggagtactt ggcttcccaa aaatgtattc      2520
atcgagattt agcagccaga atgttttggg taacagaaaa caatgtgatg aaaatagcag     2580
actttggact cgccagagat atcaacaata tagactatta caaaaagacc accaatgggc     2640
ggcttccagt caagtggatg gctccagaag ccctgtttga tagagtatac actcatcaga     2700
gtgatgtctg gtccttcggg gtgttaatgt gggagatctt cacttttaggg ggctcgccct    2760 acccagggat tccgtggag gaacttttta agctgctgaa ggaaggacac agaatggata      2820
agccagccaa ctgcaccaac gaactgtaca tgatgatgag ggactgttgg catgcagtgc     2880
cctcccagag accaacgttc aagcagttgg tagaagactt ggatcgaatt ctcactctca     2940
caaccaatga ggaatacttg gacctcagcc aacctctcga acagtattca cctagttacc     3000
ctgacacaag aagttcttgt tcttcaggag atgattctgt ttttttctcca gaccccatgc    3060
```

```
cttacgaacc atgccttcct cagtatccac acataaacgg cagtgttaaa acatgaatga   3120
ctgtgtctgc ctgtccccaa acaggacagc actgggaacc tagctacact gagcagggag   3180
accatgcctc ccagagcttg ttgtctccac ttgtatatat ggatcagagg agtaaataat   3240
tggaaaagta atcagcatat gtgtaaagat ttatacagtt gaaaacttgt aatcttcccc   3300
aggaggagaa gaaggtttct ggagcagtgg actgccacaa gccaccatgt aacccctctc   3360
acctgccgtg cgtactggct gtggaccagt aggactcaag gtggacgtgc gttctgcctt   3420
ccttgttaat tttgtaataa ttggagaaga tttatgtcag cacacactta cagagcacaa   3480
atgcagtata taggtgctgg atgtatgtaa atatattcaa attatgtata aatatatatt   3540
atatatttac aaggagttat tttttgtatt gattttaaat ggatgtccca atgcacctag   3600
aaaattggtc tctctttttt taatagctat ttgctaaatg ctgttcttac acataatttc   3660
ttaattttca ccgagcagag gtggaaaaat acttttgctt tcagggaaaa tggtataacg   3720
ttaatttatt aataaattgg taatatacaa aacaattaat catttatagt tttttttgta   3780
atttaagtgg catttctatg caggcagcac agcagactag ttaatctatt gcttggactt   3840
aactagttat cagatccttt gaaaagagaa tatttacaat atatgactaa tttggggaaa   3900
atgaagtttt gatttatttg tgtttaaatg ctgctgtcag acgattgttc ttagacctcc   3960
taaatgcccc atattaaaag aactcattca taggaaggtg tttcattttg gtgtgcaacc   4020
ctgtcattac gtcaacgcaa cgtctaactg gacttcccaa gataaatggt accagcgtcc   4080
tcttaaaaga tgccttaatc cattccttga ggacagacct tagttgaaat gatagcagaa   4140
tgtgcttctc tctggcagct ggccttctgc ttctgagttg cacattaatc agattagcct   4200
gtattctctt cagtgaattt tgataatggc ttccagactc tttggcgttg gagacgcctg   4260
ttaggatctt caagtcccat catagaaaat tgaaacacag agttgttctg ctgatagttt   4320
tggggatacg tccatctttt taagggattg ctttcatcta attctggcag gacctcacca   4380
aaagatccag cctcatacct acatcagaca aaatatcgcc gttgttcctt ctgtactaaa   4440
gtattgtgtt ttgctttgga aacacccact cactttgcaa tagccgtgca agatgaatgc   4500
agattacact gatcttatgt gttacaaaat tggagaaagt atttaataaa acctgttaat   4560
ttttatactg acaataaaaa tgtttctaca gatattaatg ttaacaagac aaaataaatg   4620
tcacgcaact taaaaaaaaa aaaaaaa                                       4647
```

<210> SEQ ID NO 2
<211> LENGTH: 822
<212> TYPE: PRT
<213> ORGANISM: Homo sapiens

<400> SEQUENCE: 2

```
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
```

```
             85                  90                  95
Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
            115                 120                 125

Ser Ser Gly Asp Asp Glu Asp Thr Asp Gly Ala Glu Asp Phe Val
        130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
                180                 185                 190

Lys Asn Gly Lys Glu Phe Lys Gln Glu His Arg Ile Gly Gly Tyr Lys
                195                 200                 205

Val Arg Asn Gln His Trp Ser Leu Ile Met Glu Ser Val Val Pro Ser
            210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
                260                 265                 270

Asp Val Glu Phe Val Cys Lys Val Tyr Ser Asp Ala Gln Pro His Ile
                275                 280                 285

Gln Trp Ile Lys His Val Glu Lys Asn Gly Ser Lys Tyr Gly Pro Asp
            290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
                340                 345                 350

Ala Trp Leu Thr Val Leu Pro Lys Gln Gln Ala Pro Gly Arg Glu Lys
                355                 360                 365

Glu Ile Thr Ala Ser Pro Asp Tyr Leu Glu Ile Ala Ile Tyr Cys Ile
            370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
                420                 425                 430

Ala Glu Ser Ser Ser Ser Met Asn Ser Asn Thr Pro Leu Val Arg Ile
                435                 440                 445

Thr Thr Arg Leu Ser Ser Thr Ala Asp Thr Pro Met Leu Ala Gly Val
            450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu Ala
                500                 505                 510
```

```
Val Thr Val Ala Val Lys Met Leu Lys Asp Asp Ala Thr Glu Lys Asp
            515                 520                 525

Leu Ser Asp Leu Val Ser Glu Met Glu Met Met Lys Met Ile Gly Lys
        530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
            580                 585                 590

Arg Val Pro Glu Glu Gln Met Thr Phe Lys Asp Leu Val Ser Cys Thr
        595                 600                 605

Tyr Gln Leu Ala Arg Gly Met Glu Tyr Leu Ala Ser Gln Lys Cys Ile
    610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
        675                 680                 685

Ser Phe Gly Val Leu Met Trp Glu Ile Phe Thr Leu Gly Gly Ser Pro
    690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
        755                 760                 765

Glu Tyr Leu Asp Leu Ser Gln Pro Leu Glu Gln Tyr Ser Pro Ser Tyr
    770                 775                 780

Pro Asp Thr Arg Ser Ser Cys Ser Ser Gly Asp Asp Ser Val Phe Ser
785                 790                 795                 800

Pro Asp Pro Met Pro Tyr Glu Pro Cys Leu Pro Gln Tyr Pro His Ile
                805                 810                 815

Asn Gly Ser Val Lys Thr
            820

<210> SEQ ID NO 3
<211> LENGTH: 821
<212> TYPE: PRT
<213> ORGANISM: Homo sapiens

<400> SEQUENCE: 3

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
```

-continued

```
                50                  55                  60
Lys Asp Ala Ala Val Ile Ser Trp Thr Lys Asp Gly Val His Leu Gly
 65                  70                  75                  80

Pro Asn Asn Arg Thr Val Leu Ile Gly Glu Tyr Leu Gln Ile Lys Gly
                 85                  90                  95

Ala Thr Pro Arg Asp Ser Gly Leu Tyr Ala Cys Thr Ala Ser Arg Thr
                100                 105                 110

Val Asp Ser Glu Thr Trp Tyr Phe Met Val Asn Val Thr Asp Ala Ile
                115                 120                 125

Ser Ser Gly Asp Asp Glu Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
                180                 185                 190

Lys Asn Gly Lys Glu Phe Lys Gln Glu His Arg Ile Gly Gly Tyr Lys
                195                 200                 205

Val Arg Asn Gln His Trp Ser Leu Ile Met Glu Ser Val Val Pro Ser
210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
                260                 265                 270

Asp Val Glu Phe Val Cys Lys Val Tyr Ser Asp Ala Gln Pro His Ile
                275                 280                 285

Gln Trp Ile Lys His Val Glu Lys Asn Gly Ser Lys Tyr Gly Pro Asp
290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
                340                 345                 350

His Ser Ala Trp Leu Thr Val Leu Pro Ala Pro Gly Arg Glu Lys Glu
                355                 360                 365

Ile Thr Ala Ser Pro Asp Tyr Leu Glu Ile Ala Ile Tyr Cys Ile Gly
370                 375                 380

Val Phe Leu Ile Ala Cys Met Val Val Thr Val Ile Leu Cys Arg Met
385                 390                 395                 400

Lys Asn Thr Thr Lys Lys Pro Asp Phe Ser Ser Gln Pro Ala Val His
                405                 410                 415

Lys Leu Thr Lys Arg Ile Pro Leu Arg Arg Gln Val Thr Val Ser Ala
                420                 425                 430

Glu Ser Ser Ser Ser Met Asn Ser Asn Thr Pro Leu Val Arg Ile Thr
                435                 440                 445

Thr Arg Leu Ser Ser Thr Ala Asp Thr Pro Met Leu Ala Gly Val Ser
450                 455                 460

Glu Tyr Glu Leu Pro Glu Asp Pro Lys Trp Glu Phe Pro Arg Asp Lys
465                 470                 475                 480
```

-continued

Leu Thr Leu Gly Lys Pro Leu Gly Glu Gly Cys Phe Gly Gln Val Val
            485                 490                 495

Met Ala Glu Ala Val Gly Ile Asp Lys Asp Lys Pro Lys Glu Ala Val
            500                 505                 510

Thr Val Ala Val Lys Met Leu Lys Asp Asp Ala Thr Glu Lys Asp Leu
            515                 520                 525

Ser Asp Leu Val Ser Glu Met Glu Met Met Lys Met Ile Gly Lys His
530                 535                 540

Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
                565                 570                 575

Arg Ala Arg Arg Pro Pro Gly Met Glu Tyr Ser Tyr Asp Ile Asn Arg
            580                 585                 590

Val Pro Glu Glu Gln Met Thr Phe Lys Asp Leu Val Ser Cys Thr Tyr
            595                 600                 605

Gln Leu Ala Arg Gly Met Glu Tyr Leu Ala Ser Gln Lys Cys Ile His
            610                 615                 620

Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
                660                 665                 670

Glu Ala Leu Phe Asp Arg Val Tyr Thr His Gln Ser Asp Val Trp Ser
            675                 680                 685

Phe Gly Val Leu Met Trp Glu Ile Phe Thr Leu Gly Gly Ser Pro Tyr
            690                 695                 700

Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
                725                 730                 735

Arg Asp Cys Trp His Ala Val Pro Ser Gln Arg Pro Thr Phe Lys Gln
            740                 745                 750

Leu Val Glu Asp Leu Asp Arg Ile Leu Thr Leu Thr Thr Asn Glu Glu
            755                 760                 765

Tyr Leu Asp Leu Ser Gln Pro Leu Glu Gln Tyr Ser Pro Ser Tyr Pro
            770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
            820

<210> SEQ ID NO 4
<211> LENGTH: 21
<212> TYPE: DNA
<213> ORGANISM: Artificial Sequence
<220> FEATURE:
<223> OTHER INFORMATION: Artificial Sequence shRNA targeting exon 2 of
      FGFR2

<400> SEQUENCE: 4
ttagttgagg ataccacatt a                                              21

<210> SEQ ID NO 5
<211> LENGTH: 19
<212> TYPE: DNA
<213> ORGANISM: Artificial Sequence
<220> FEATURE:
<223> OTHER INFORMATION: Artificial Sequence shRNA targeting exon 15 of
      FGFR2

<400> SEQUENCE: 5
atgtattcat cgagattta                                                    19

<210> SEQ ID NO 6
<211> LENGTH: 21
<212> TYPE: DNA
<213> ORGANISM: Artificial Sequence
<220> FEATURE:
<223> OTHER INFORMATION: Artificial Sequence A non-silencing shRNA

<400> SEQUENCE: 6
aattctccga acgtgtcacg t                                                 21

<210> SEQ ID NO 7
<211> LENGTH: 4644
<212> TYPE: DNA
<213> ORGANISM: Homo sapiens

<400> SEQUENCE: 7
ggcggcggct ggaggagagc gcggtggaga gccgagcggg cgggcggcgg gtgcggagcg        60
ggcgagggag cgcgcgcggc cgccacaaag ctcgggcgcc gcggggctgc atgcggcgta       120
cctggcccgg cgcggcgact gctctccggg ctggcggggg ccggccgcga gccccggggg       180
ccccgaggcc gcagcttgcc tgcgcgctct gagccttcgc aactcgcgag caaagtttgg       240
tggaggcaac gccaagcctg agtcctttct tcctctcgtt ccccaaatcc gagggcagcc       300
cgcgggcgtc atgcccgcgc tcctccgcag cctggggtac cgcgtgaagc cgggaggctt       360
ggcgccggcg aagacccaag gaccactctt ctgcgtttgg agttgctccc cgcaaccccg       420
ggctcgtcgc tttctccatc ccgacccacg cggggcgcgg gacaacacac ggtcgcggag       480
gagcgttgcc attcaagtga ctgcagcagc agcggcagcg cctcggttcc tgagcccacc       540
gcaggctgaa ggcattgcgc gtagtccatg cccgtagagg aagtgtgcag atgggattaa       600
cgtccacatg gagatatgga agaggaccgg ggattggtac cgtaaccatg gtcagctggg       660
gtcgtttcat ctgcctggtc gtggtcacca tggcaacctt gtccctggcc ggccctcct       720 tcagtttagt tgaggatacc acattagagc cagaagagcc accaaccaaa taccaaatct       780
ctcaaccaga agtgtacgtg gctgcgccag gggagtcgct agaggtgcgc tgcctgttga       840
aagatgccgc cgtgatcagt tggactaagg atggggtgca cttggggccc aacaatagga       900
cagtgcttat tggggagtac ttgcagataa agggcgccac gcctagagac tccggcctct       960
atgcttgtac tgccagtagg actgtagaca gtgaaacttg gtacttcatg gtgaatgtca      1020
cagatgccat ctcatccgga gatgatgagg atgacaccga tggtgcggaa gattttgtca      1080
gtgagaacag taacaacaag agagcaccat actggaccaa cacagaaaag atggaaaagc      1140
ggctccatgc tgtgcctgcg ccaacactg tcaagtttcg ctgcccagcc gggggggaacc     1200 caatgccaac catgcggtgg ctgaaaaacg gaaggagtt taagcaggag catcgcattg      1260
gaggctacaa ggtacgaaac cagcactgga gcctcattat ggaaagtgtg gtcccatctg      1320
acaagggaaa ttatacctgt gtagtggaga tgaatacgg gtccatcaat cacacgtacc      1380

```
acctggatgt tgtggagcga tcgcctcacc ggcccatcct ccaagccgga ctgccggcaa   1440
atgcctccac agtggtcgga ggagacgtag agtttgtctg caaggtttac agtgatgccc   1500
agccccacat ccagtggatc aagcacgtgg aaaagaacgg cagtaaatac gggcccgacg   1560
ggctgcccta cctcaaggtt ctcaaggccg ccggtgttaa caccacggac aaagagattg   1620
aggttctcta tattcggaat gtaacttttg aggacgctgg ggaatatacg tgcttggcgg   1680
gtaattctat tgggatatcc tttcactctg catggttgac agttctgcca cgcctggaa    1740 gagaaaagga gattacagct tccccagact acctggagat agccatttac tgcataggg    1800 tcttcttaat cgcctgtatg gtggtaacag tcatcctgtg ccgaatgaag aacacgacca   1860
agaagccaga cttcagcagc cagccggctg tgcacaagct gaccaaacgt atcccctgc    1920 ggagacaggt aacagtttcg gctgagtcca gctcctccat gaactccaac accccgctgg   1980
tgaggataac aacacgcctc tcttcaacgg cagacacccc catgctggca ggggtctccg   2040
agtatgaact tccagaggac ccaaaatggg agtttccaag agataagctg acactgggca   2100
agcccctggg agaaggttgc tttgggcaag tggtcatggc ggaagcagtg ggaattgaca   2160 aagcaagcc caaggaggcg gtcaccgtgg ccgtgaagat gttgaaagat gatgccacag    2220
agaaagacct ttctgatctg gtgtcagaga tggagatgat gaagatgatt gggaaacaca   2280
agaatatcat aaatcttctt ggagcctgca cacaggatgg gcctctctat gtcatagttg   2340
agtatgcctc taaaggcaac ctccgagaat acctccgagc ccggaggcca cccgggatgg   2400
agtactccta tgacattaac cgtgttcctg aggagcagat gaccttcaag gacttggtgt   2460
catgcaccta ccagctggcc agaggcatgg agtacttggc ttcccaaaaa tgtattcatc   2520
gagatttagc agccagaaat gttttggtaa cagaaaacaa tgtgatgaaa atagcagact   2580
ttggactcgc cagagatatc aacaatatag actattacaa aaagaccacc aatgggcggc   2640
ttccagtcaa gtggatggct ccagaagccc tgtttgatag agtatacact catcagagtg   2700
atgtctggtc cttcggggtg ttaatgtggg agatcttcac tttaggggc tcgccctacc    2760 cagggattcc cgtggaggaa cttttttaagc tgctgaagga aggacacaga atggataagc   2820
cagccaactg caccaacgaa ctgtacatga tgatgaggga ctgttggcat gcagtgccct   2880
cccagagacc aacgttcaag cagttggtag aagacttgga tcgaattctc actctcacaa   2940
ccaatgagga atacttggac ctcagccaac ctctcgaaca gtattcacct agttaccctg   3000
acacaagaag ttcttgttct tcaggagatg attctgtttt ttctccagac cccatgcctt   3060
acgaaccatg ccttcctcag tatccacaca taaacggcag tgttaaaaca tgaatgactg   3120
tgtctgcctg tccccaaaca ggacagcact gggaacctag ctacactgag cagggagacc   3180
atgcctccca gagcttgttg tctccacttg tatatatgga tcagaggagt aaataattgg   3240
aaaagtaatc agcatatgtg taaagattta tacagttgaa aacttgtaat cttccccagg   3300
aggagaagaa ggtttctgga gcagtggact gccacaagcc accatgtaac ccctctcacc   3360
tgccgtgcgt actggctgtg gaccagtagg actcaaggtg gacgtgcgtt ctgccttcct   3420
tgttaatttt gtaataattg gagaagattt atgtcagcac acacttacag agcacaaatg   3480
cagtatatag gtgctggatg tatgtaaata tattcaaatt atgtataaat atatattata   3540
tatttacaag gagttatttt ttgtattgat tttaaatgga tgtcccaatg cacctagaaa   3600
attggtctct cttttttttaa tagctatttg ctaaatgctg ttcttacaca taatttctta   3660
attttcaccg agcagaggtg gaaaaatact tttgctttca gggaaaatgg tataacgtta   3720
```

```
atttattaat aaattggtaa tatacaaaac aattaatcat ttatagtttt ttttgtaatt    3780
taagtggcat ttctatgcag gcagcacagc agactagtta atctattgct tggacttaac    3840
tagttatcag atcctttgaa aagagaatat ttacaatata tgactaattt ggggaaaatg    3900 aagtttgat ttatttgtgt ttaaatgctg ctgtcagacg attgttctta gacctcctaa     3960
atgccccata ttaaaagaac tcattcatag gaaggtgttt cattttggtg tgcaaccctg    4020
tcattacgtc aacgcaacgt ctaactggac ttcccaagat aaatggtacc agcgtcctct    4080
taaaagatgc cttaatccat tccttgagga cagaccttag ttgaaatgat agcagaatgt    4140
gcttctctct ggcagctggc cttctgcttc tgagttgcac attaatcaga ttagcctgta    4200
ttctcttcag tgaattttga taatggcttc cagactcttt ggcgttggag acgcctgtta    4260
ggatcttcaa gtcccatcat agaaaattga aacacagagt tgttctgctg atagttttgg    4320
ggatacgtcc atcttttta gggattgctt tcatctaatt ctggcaggac ctcaccaaaa     4380
gatccagcct catacctaca tcagacaaaa tatcgccgtt gttccttctg tactaaagta    4440
ttgtgttttg ctttggaaac acccactcac tttgcaatag ccgtgcaaga tgaatgcaga    4500
ttacactgat cttatgtgtt acaaaattgg agaaagtatt taataaaacc tgttaatttt    4560
tatactgaca ataaaaatgt ttctacagat attaatgtta acaagacaaa ataaatgtca    4620
cgcaacttaa aaaaaaaaaa aaaa                                           4644
```

METHODS OF DIAGNOSING, CLASSIFYING AND TREATING ENDOMETRIAL CANCER AND PRECANCER

CROSS-REFERENCE TO RELATED PATENT APPLICATIONS

This patent application is a continuation of U.S. application Ser. No. 13/973,614, filed Aug. 22, 2013 (abandoned on May 27, 2016), which is a continuation-in-part of U.S. application Ser. No. 12/532,563 filed Nov. 11, 2009 (abandoned on Dec. 15, 2013), which is a National Stage Entry of International Patent Application No. PCT/US2008/058065 filed Mar. 24, 2008 (expired), which claims priority to U.S. provisional application Ser. No. 60/896,884, filed Mar. 23, 2007 and U.S. provisional application Ser. No. 60/982,093, filed Oct. 23, 2007. Each of the foregoing applications is hereby incorporated by reference in its entirety.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 27,199 byte ASCII (text) file named "Seq_list" created on Aug. 22, 2013.

FIELD OF THE INVENTION

The present invention is directed to methods and kits for diagnosing, classifying, and treating endometrial cancer.

BACKGROUND OF THE INVENTION

Endometrial cancer is the most commonly diagnosed malignancy of the female reproductive tract in the United States. It was estimated that 39,080 new cases of cancer of the uterine corpus would be diagnosed and 7,400 women would die of this disease in the United States in 2007 (Jemal A, Siegel R, Ward E, Murray T, Xu J, Thun M J. CA Cancer J Clin 2007 January-February; 57(1):43-66). The majority of women presenting with endometrial cancer are surgically cured with a hysterectomy; however, about 15% of women demonstrate persistent or recurrent tumors that are refractory to current chemotherapies. For those women with advanced stage, progressive, or recurrent disease, survival is poor as there are no adjuvant therapies proven to be effective. The median survival after recurrence is ten months (Jereczek-Fossa B, Badzio A, Jassem J., Int J Gynecol Cancer 1999 July; 9(4):285-94) and the five-year survival for patients who have recurred is only 13% (Creutzberg C L, van Putten W L, Koper P C, et al., Lancet 2000 Apr. 22; 355(9213): 1404-11).

Malignant carcinomas often display mutations in multiple oncogenes and tumor suppressor genes, exhibit alterations in the expression of hundreds of genes, and contain various chromosomal abnormalities. Despite this genomic complexity, targeting specific molecular abnormalities has been shown to produce rapid regression of human tumors, such as is seen with the selective tyrosine kinase inhibitors Imatinib (Gleevec) and Gefitinib (Iressa). To explain this phenomenon, Bernard Weinstein introduced the term "oncogene addiction". He proposed that the signaling circuitry of a tumor cell is reprogrammed in the presence of an oncogenic activity such that the tumor cell is dependent on that oncogenic activity for cell survival and growth (Weinstein I B. Science 2002 Jul. 5; 297(5578):63-4). Indeed, experimental and clinical data support this concept of oncogene addiction and, furthermore, suggest that multiple mechanisms of oncogene activation, including mutation, rearrangement, and overexpression, can be involved in oncogene addiction (Weinstein I B, Joe A K., Nat Clin Pract Oncol 2006 August; 3(8):448-57).

A variety of somatic gene defects have been reported in endometrial carcinoma. Well or moderately differentiated endometrioid endometrial carcinomas account for approximately 80% of uterine cancers. They are characterized by a high frequency of inactivating mutations in PTEN (26-80%), activating KRAS2 mutations (13-26%), and gain-of-function β-catenin mutations (25-38%) (Hecht J L, Mutter G L., J Clin Oncol 2006 Oct. 10; 24(29):4783-91, Shiozawa T, Konishi I., Int J Clin Oncol 2006 February; 11(1):13-21). Germline gain-of-function mutations in FGFR1, 2, and 3 have been reported in a variety of craniosynostosis syndromes and chondrodysplasia syndromes. The genotype/phenotype correlations in these disorders are complex, with over 14 distinct clinical syndromes associated with mutations in one of the three receptors and several clinical syndromes e.g., Pfeiffer and Crouzon Syndrome associated with mutations in different receptors (Passos-Bueno M R, Wilcox W R, Jabs E W, Sertie A L, Alonso L G and Kitoh H. (1999), Hum Mutat 14: 115-125, Wilkie A O, Patey S J, Kan S H, van den Ouweland A M and Hamel B C. (2002), Am J Med Genet 112: 266-278).

Although much progress has been made toward understanding the biological basis of cancer and in its diagnosis and treatment, it is still one of the leading causes of death in the United States. Inherent difficulties in the diagnosis and treatment of cancer include among other things, the existence of many different subgroups of cancer and the concomitant variation in appropriate treatment strategies to maximize the likelihood of positive patient outcome. Furthermore, there are a wide range of endometrial cancer subgroups and variations in the disease's progression. To properly treat the endometrial cancer and to maximize the chances of a successful treatment it is important that the type or subtype of endometrial cancer be identified as early as possible.

Thus, there presently is a need for a method of detecting and classifying endometrial cancer in order to select the appropriate and optimal treatment regimen. Once detected and classified, there is a further need for improved methods of treating endometrial cancer based on the type of endometrial cancer to maximize the chances of successfully treating or inhibiting reoccurrence of the disease in the subject.

SUMMARY OF THE INVENTION

The present invention provides methods of diagnosing, classifying and treating endometrial cancer. By identifying and correlating fibroblast growth factor receptor 2 (FGFR2) activation mutations with endometrial cancer, the inventors herein provide useful tools for diagnosing, classifying, and treating endometrial cancer in a subject.

In one embodiment, the present invention is a method of detecting and diagnosing endometrial cancer or precancer in a subject, preferably a human subject. The method preferably comprises detecting a receptor mutation in a FGFR2 in a biological sample containing endometrial cells, wherein the mutation is associated with FGFR2 receptor activation. The presence of one or more activation mutations in the FGFR2 is diagnostic of endometrial cancer or precancer in the subject. The activation mutation can be a missense mutation, a deletion, an insertion, and both a deletion and an insertion and often result in enhanced ligand binding, promiscuous ligand binding (e.g, allows the receptor to bind to and be activated by ligands that cannot normally bind to the wildtype receptor) constitutive receptor dimerization, impaired receptor recycling leading to augmentation of signaling, delayed degradation, overexpression, or kinase activation. In a preferred embodiment, the FGFR2 is a constitutively active mutant, which may still require ligand stimulation for optimal signaling.

Preferably, the step of detecting comprises screening the biological sample for at least one nucleotide FGFR2 mutation in at least one nucleic acid of genomic DNA, RNA, or cDNA. In certain embodiments the activation mutation results in an at least one amino acid substitution in FGFR2.

In a preferred embodiment the FGFR2 activation mutation includes at least one mutation selected from the group consisting of: a mutation in the junction between the immunoglobulin-like (Ig) domains II and III (e.g., a S to W, F, or L mutation at position 252; a P to R mutation at position 253; a P to L mutation at position 263; a S to P mutation at position 267, all of SEQ ID NOS:2 or 3); a mutation in the IgIII domain (e.g., a F to V mutation at position 276; a C to Y or F mutation at position 278; a Y to C mutation at position 281; an I to S mutation at position 288; a Q to P mutation at position 289; a Y to C, G. or R mutation at position 290; a K to E mutation at position 292; a K to R mutation at position 310; an A to T mutation at position 315; a D to A mutation at position 321; a Y to C mutation at position 328, all of SEQ ID NOS:2 or 3); a mutation in the junction between the IgIII domain and the transmembrane (TM) domain (e.g., a S to C or T mutation at position 354 or 353; a V to F mutation at position 359 or 358; an A to S mutation at position 362 or 361; a S to C mutation at position 372 or 371; a Y to C mutation at position 375 or 374; a S to C mutation at position 373 or 372; a Y to C mutation at position 376 or 375, all of SEQ ID NOS:2 or 3 respectively); a mutation of the TM domain (e.g., a G to R mutation at position 380 or 379; a C to R mutation at position 383 or 382; a G to R mutation at positions 384 or 383; a M to R mutation at position 392 or 391, all of SEQ ID NOS: 2 or 3 respectively); a mutation in the junction between the TM domain and the tyrosine kinase domain I (e.g., an IVS10+ 2A>C splicing mutation); a mutation in the tyrosine kinase domain I (e.g., an I to V mutation at position 538 or 537; a N to K mutation at position 540; an I to V mutation at position 548 or 547; a N to H mutation at position 549 or 548; a N to K mutation at position 550 or 549; an E to G mutation at position 565 or 564, all of SEQ ID NOS:2 or 3 respectively); or a mutation in the tyrosine kinase domain II (e.g., a K to R mutation at position 641 or 640; a K to E mutation at position 650 or 649; a K to N mutation at position 659 or 658; a K to E mutation at position 660 or 659; a G to E mutation at position 663 or 662; a R to G mutation at position 678 or 677, all of SEQ ID NOS:2 or 3 respectively; a frame shift mutation caused by the deletion of nucleotide C and T at position 2290-91 of SEQ ID NO:1).

Other examples of preferred activation mutations of the IgIII domain include for example, a N to I mutation at position 331; an A to P mutation at position 337, a G to P or R mutation at position 338; a Y to C or H mutation at position 340; a T to P mutation at position 341; a C to F, G, R, S, W or Y mutation at position 342; an A to G or P mutation at position 344; a S to C mutation at position 347; a S to C mutation at position 351, all of SEQ ID NO:2, and the equivalent mutations in SEQ ID NO:3.

It is important to note that more than one FGFR2 activation mutation may be detected in a biological sample, for example, at least two FGFR2 receptor activation mutations are detected in certain embodiments.

The endometrial cancer detected can be any subtypes, for example, serous, mucinous, and endometrioid histological subtypes. In a preferred embodiment, however, the cancer detected is an endometrioid histologic subtype.

In addition, the invention provides a method diagnosing or classifying endometrial cancer in a subject, which comprises assessing the level of activity of a FGFR2 signal transduction pathway in a test subject and comparing it to the level of activity in a control subject, wherein increased activity of the FGFR2 pathway in the test subject compared to the control subject is indicative of endometrial cancer. The level of activity of the pathway can, for example, be assessed by assessing an increase in the level of expression or activity of a FGFR2 protein. Alternatively, the level of expression or activity may, for example, be assessed by determining the amount of mRNA that encodes the FGFR2, preferably a mutated FGFR2 that results in receptor activation. For example, in one embodiment, endometrial cancer is associated with overexpression of FGFR2 due to genomic amplification, and the assay is designed specifically to detect the overexpression of FGFR2.

The invention is also directed to a kit for diagnosing or classifying endometrial cancer, comprising an oligonucleotide that specifically hybridizes to or adjacent to a site of mutation of a FGFR2 gene that results in increased activity of a FGFR2 protein encoded by the gene, and instructions for use in diagnosing endometrial cancer. The site of mutation may, for example, comprise a nucleotide selected from the group consisting of nucleotides 755, 929, 943, 1118, 1147, 1642, 1650, 1978, and 2290-91 of SEQ ID NO:1 and the equivalent nucleotides of SEQ ID NO:7. In a preferred embodiment, the kit comprises at least one probe comprising the site of mutation.

The invention further is directed to a kit for diagnosing or classifying endometrial cancer, comprising an antibody that specifically recognizes a mutation in a FGFR2 protein, and instructions for use. Optionally, the mutation results in an increased activity as compared to a non-mutated FGFR2 protein, such as that of SEQ ID NOS:2 and 3. Preferably, the antibody is directed against a specific FGFR2 protein mutation selected from the group consisting of: a mutation in the junction between the immunoglobulin-like (Ig) domains II and III; a mutation in the IgIII domain; a mutation in the junction between the IgIII domain and the transmembrane (TM) domain; a mutation in the TM domain; a mutation in the junction between the TM domain and the tyrosine kinase domain I; a mutation in the tyrosine kinase domain I, or a mutation in the tyrosine kinase domain II. More preferably the antibody is directed to a mutation selected from the group consisting of: (a) a S to W mutation at position 252 of SEQ ID NOS:2 (NP_075259.2) or 3 (NP_000132.1); (b) a K to R mutation at position 310 of SEQ ID NOS:2 or 3; (c) an A to T mutation at position 315 of SEQ ID NOS:2 or 3; (d) a S to C mutation at position 373 of SEQ ID NO:2 or position 372 of SEQ ID NO:3; (e) a Y to C mutation at position 376 of SEQ ID NO:2 or position 375 of SEQ ID NO:3; (f) a C to R mutation at position 383 of SEQ ID NO:2 or position 382 of SEQ ID NO:3; (g) a M to R mutation at position 392 of SEQ ID NO:2 or position 391 of SEQ ID NO:3; (h) an I to V mutation at position 548 of SEQ ID NO:2 or position 547 of SEQ ID NO:3; (i) N to K mutation at position 550 of SEQ ID NO:2 or position 549 of SEQ ID NO:3; or (j) a K to E mutation at position 660 of SEQ ID NO:2 or position 659 of SEQ ID NO:3.

The present invention further provides a method of treating endometrial cancer or precancer in a subject. Preferably the subject is a human affected with endometrial cancer (e.g., serous, mucinous, and endometrioid histological subtypes). The method preferably comprises administering an effective amount of a FGFR2 inhibitor with a pharmaceutically acceptable carrier to the subject having endometrial cancer or precancer characterized by FGFR2 activation, for example, a FGFR2 mutated form that is constitutively active in either a ligand-independent or ligand-dependent manner, wherein the FGFR2 inhibitor inhibits FGFR2 expression or activity, thereby effectively inhibiting growth or proliferation of the endometrial cancer in the subject. The FGFR2 inhibitor preferably induces cell cycle arrest and/or apoptosis of the endometrial cancer cells. In one embodiment, the FGFR2 inhibitor is administered to the subject after surgical treatment for endometrial cancer to inhibit the reoccurrence of endometrial cancer after surgery. In another embodiment, the inhibitor is administered to patients with persistent or recurrent endometrial cancer, not amenable to surgical removal.

The FGFR2 inhibitor used may inhibit expression of a FGFR2 gene or a FGFR2 expression product. In one embodiment the agent is a FGFR2 antisense nucleic acid, preferably an antisense nucleic acid hybridizing to a segment of SEQ ID NO:1 comprising at least one nucleotide substitution selected from an A to G substitution at position 929; a T to G substitution at position 1650; a G to A substitution at position 943; a C to G substitution at position 755; a T to A or G substitution at position 1650; an A to G substitution at position 1127; a C to G substitution at position 1175; an A to G substitution at position 1642; an A to G substitution at position 1978; an Intron10 A>C+2; or a deletion of CT at positions 2290-91, and the equivalent substitutions of SEQ ID NO:7.

In another embodiment, the FGFR2 inhibitor inhibits FGFR2 activity by blocking a FGFR2 domain. For example, the FGFR2 inhibitor is an anti-FGFR2 inhibitory antibody directed against the linker region between the immunoglobulin-like (Ig) domains II and III of FGFR2; the IgIII domain of FGFR2; the junction between the IgIII domain and the transmembrane (TM) domain of FGFR2; the TM domain; the junction between the TM domain and the tyrosine kinase domain I of FGFR2; the tyrosine kinase domain I of FGFR2, or the tyrosine kinase domain II of FGFR2. For example, in one embodiment, the FGFR2 inhibitor interferes with the FGFR2 folding, the three dimensional structure of FGFR2, ligand binding, or substrate binding, e.g., ATP.

Preferred examples include an antibody that specifically recognizes a FGFR2 amino acid sequence comprising mutations selected from the following: (a) a S to W mutation at position 252 of SEQ ID NOS:2 (NP_075259.2) or 3 (NP_000132.1); (b) a K to R mutation at position 310 of SEQ ID NOS:2 or 3; (c) an A to T mutation at position 315 of SEQ ID NOS:2 or 3; (d) a S to C mutation at position 373 of SEQ ID NO:2 or position 372 of SEQ ID NO:3; (e) a Y to C mutation at position 376 of SEQ ID NO:2 or position 375 of SEQ ID NO:3; (f) a C to R mutation at position 383 of SEQ ID NO:2 or position 382 of SEQ ID NO:3; (g) a M to R mutation at position 392 of SEQ ID NO:2 or position 391 of SEQ ID NO:3; (h) an I to V mutation at position 548 of SEQ ID NO:2 or position 547 of SEQ ID NO:3; (i) N to K mutation at position 550 of SEQ ID NO:2 or position 549 of SEQ ID NO:3; or (j) a K to E mutation at position 660 of SEQ ID NO:2 or position 659 of SEQ ID NO:3.

In a preferred embodiment, the antibody is directed against a S to W mutation at position 252 of SEQ ID NOS:2 or 3. In another preferred embodiment the antibody is a humanized antibody and preferably a monoclonal antibody.

In an alternative embodiment, the FGFR2 inhibitor is a small inhibitory RNA (siRNA), a small hairpin RNA (shRNA), microRNA (miRNA), or a ribozyme. In a preferred embodiment the FGFR2 inhibitor is a shRNA, preferably a shRNA that targets exon 2 of FGFR2 (SEQ ID NO:4) and/or exon 15 of FGFR2 (SEQ ID NO:5). In another specific nonlimiting embodiment, the FGFR2 inhibitor is PD173074.

The invention further provides a method of classifying endometrial cancer. The method allows a user to properly classify the type of endometrial cancer so that a specific and proper treatment can be used based on the type of endometrial cancer a subject has. The method comprises: screening for a FGFR2 mutation in an endometrial cancer cell; and classifying the type of endometrial cancer as a FGFR2 activation induced endometrial cancer upon finding a FGFR2 activation mutation in the endometrial cancer cell. Preferably the FGFR2 activation mutation is one or more of the FGFR2 mutation identified above. In certain embodiments, the method further comprises determining if the FGFR2 mutation induces FGFR2 activation.

BRIEF DESCRIPTION OF THE DRAWINGS

FIGS. 1A and 1B show the effect of FGFR2 shRNA on cell proliferation of endometrial cancer cells. AN3CA (FIG. 1A) or MFE296 (FIG. 1B) cells were transduced with empty vector, nonsilencing, or two independent FGFR2 shRNA constructs targeting two different exons of FGFR2 (X2 or X15) and the effect on cell proliferation assessed using the SRB assay. Treatment with FGFR2 shRNA suppressed proliferation of both cell lines. Nonsilencing control shRNA had no effect on cell proliferation. FIG. 1C. Effect of FGFR2 knockdown on activation of ERK1/2 and AKT. Following shRNA transduction, AN3CA cells were serum starved in 0.2% FBS for 18 hours or maintained in full growth media containing 10% FBS. Lysates were collected and analyzed by Western blot for FGFR2 expression and activation of ERK1/2 and AKT. Knockdown of FGFR2 resulted in reduced ERK1/2 activation in 0.2% and 10% FBS, a modest reduction in AKT phosphorylation in 10% FBS, and had no effect on AKT activation in 0.2% FBS. FIG. 1D. Cell death following knockdown of FGFR2. AN3CA cells were transfected with nonsilencing siRNA (NS) control or FGFR2 siRNA X2 using Lipofectamine 2000 transfection reagent. 48 hours after transfection, cells were collected, stained with 500 ng/mL Annexin V-FITC and 1 µg/mL propidium iodide, and analyzed for Annexin-FITC positive cells by flow cytometry. Knockdown of FGFR2 resulted in an increase in Annexin V positive cells, indicative of apoptosis. 30 µg of total protein lysates were analyzed by western blot analysis to confirm FGFR2 knockdown. This knockdown was achieved with siRNAs rather than the shRNA constructs as the latter also expressed GFP, which has an overlapping emission spectra with FITC. FIG. 1E shows the PTEN expression in endometrial cancer cell lines. Endometrial cancer cell lysates were collected and evaluated by Western blot analysis for PTEN expression.

FIG. 2B shows the activation status of PLCg following PD173074 treatment.

Cells were serum-starved in 0.2% FBS for 18 hours, and then treated with increasing concentrations of PD173074 for three hours. Lysates were collected and evaluated by Western blot analysis for activation of PLCg. FIG. 2C shows cell proliferation in the absence of and in response to FGF2. The constitutively active FGFR2 kinase domain mutation N550K results in an increase in proliferation over that induced by the wild type receptor (WT) both in the absence (−FGF2) of and in the presence (+FGF2) of exogenous FGF2 ligand. These data suggest that whilst the N550K mutation is constitutively active, it also requires ligand for full activity.

(FIG. 3A) Annexin staining reveals cell death of AN3CA cells following treatment with the pan-FGFR inhibitor, PD173074. AN3CA cells plated at a density of $2.5 \times 10^5$ cells/well were treated with DMSO (vehicle control) or 1 µM PD173074. 48, 72, or 96 hours later, cells were collected, stained with 500 ng/mL annexin-FITC and 1 ug/mL propidium iodide, and analyzed in triplicate for annexin positive cells by flow cytometry. PD173074 treated cells showed an increase in Annexin-V staining compared to cells treated with DMSO alone, indicative of apoptosis. (FIG. 3B) PD173074 leads to G1 cell cycle arrest in AN3CA cells. Cells were plated in triplicate in 6 well plates and treated with 1 µM PD173074. Cell cycle was measured by propidium iodide staining and flow cytometry 72 hrs following addition of PD173074.

FIGS. 5A-B. Activation status of key signaling molecules over time following PD173074 treatment. (FIG. 5A) Cells were treated with 1 µM PD173074 in 10% FBS for the indicated times of 0 to 72 hours. Lysates were collected and evaluated by Western blot analysis for activation of ERK1/2, AKT, STAT3, and p38. PD173074 treatment resulted in suppression of ERK1/2 activation and partial suppression of AKT phosphorylation, but had no effect on STAT3 or p38 activation in AN3CA and MFE296 cells. PD173074 had no effect on ERK1/2, AKT, STAT3/5, or p38 activation in HEC1A cells. (FIG. 5B) Cells were starved in 0.2% FBS overnight and then treated with 1 µM PD173074 in 0.2% FBS for the indicated times of 0 to 72 hours. Lysates were collected and evaluated by Western blot analysis for activation of ERK1/2, AKT, STAT3, and p38. PD173074 treatment resulted in suppression of ERK1/2 activation and modest suppression of AKT phosphorylation in AN3CA and MFE296 cells. PD173074 had no effect on ERK1/2 or AKT activation in HEC1A cells.

DETAILED DESCRIPTION OF THE PREFERRED EMBODIMENTS

The invention will now be described in reference to the preferred embodiments of the invention for purposes of illustration only. It will be understood by one skilled in the art that numerous modifications or alterations may be made in and to the illustrated embodiments without departing from the spirit and scope of the invention.

The invention, in part, is based on the discovery that mutations in the FGFR2 receptor that induce receptor activation can be used to effectively detect and classify endometrial cancer or precancer in a subject. The present invention is further based on the discovery that inhibition of the FGFR2 gene or its expression products are effective in treating endometrial cancer.

As used herein the term "endometrial cancer" encompasses all forms and subtypes of the disease, including for example, serous, mucinous, and endometrioid histological subtypes. Endometrial cancer is cancer that starts in the endometrium, the lining of the uterus (womb).

Figure 6:
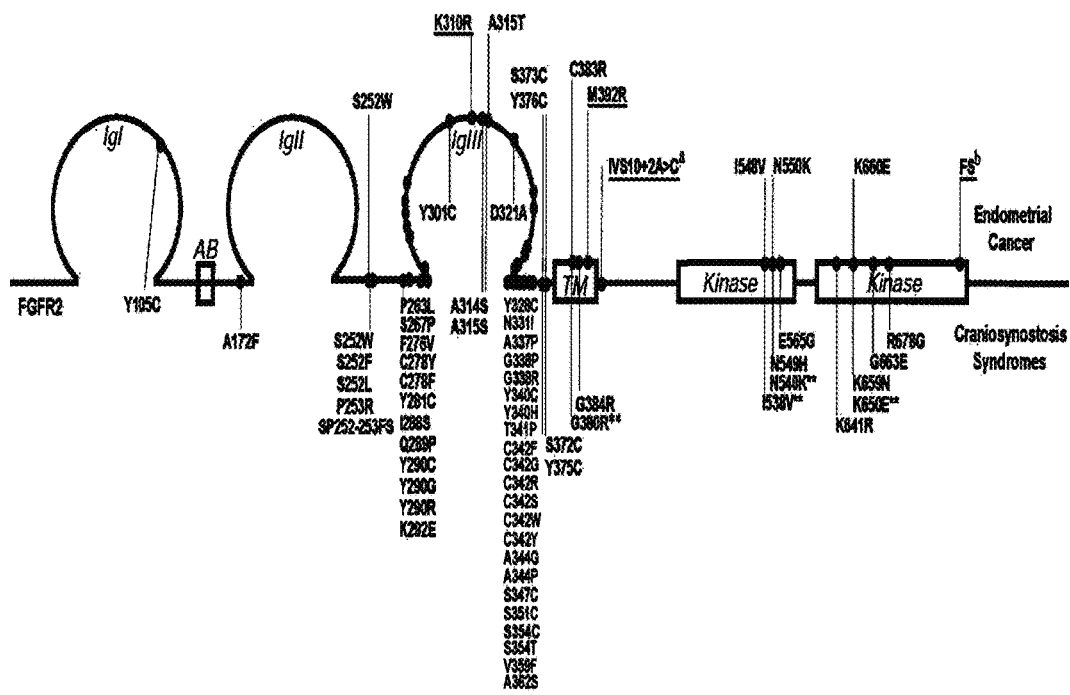
FIG. 6 is a schematic representation of FGFR2 mutations. The FGFR2 mutation are mapped to functional domains. Somatic mutations identified in primary endometrial cancers and cell lines are presented above the schematic representation of the protein and are numbered relative to FGFR2b (SEQ ID NO:2; NP_075259.2). Germline mutations associated with a variety of craniosynostosis syndromes and numbered relative to FGFR2c (SEQ ID NO:3 NP_000132.1). Four somatic FGFR2 endometrial mutations, while not previously reported in the germline, have an identical missense change reported in the paralogous position in FGFR3c in a skeletal chondrodysplasia (indicated with **). Novel mutations are underlined. $^a$The IVS10+ 2A>C mutation likely results in a relative increase in the proportion of the +VT spliceform. $^b$FS refers to a 2 bp deletion 2290-91 CT resulting in a frameshift and premature truncation.

In context of the present invention, the FGFR2 gene encompasses a gene, preferably of human origin, a coding nucleotide sequence set forth in SEQ ID NOS:1, 7, or homologs including allelic variants and orthologs. The FGFR2 protein encompasses a protein, also preferably of human origin, having the amino acid sequence set forth in SEQ ID NOS:2 or 3, or homologs, including orthologs thereof. FIG. 6 shows the functional domains of the FGFR2 domains of the FGFR2 protein and the FGFR2 mutations mapped in relation with the functional domains.

FGFR2 belongs to a family of structurally related tyrosine kinase receptors (FGFRs 1-4) encoded by four different genes. FGFR2 is a glycoprotein composed of three extracellular immunoglobulin-like (Ig) domains, a transmembrane domain, and a split tyrosine kinase domain. Alternative splicing in the IgIII domain is primary determinant of both the patterns of redundany and specificity in FGF/FGFR binding and signaling. This splicing event is tissue specific and gives rise to the IIIb and IIIc receptor isoforms for FGFR1-FGFR3 which possess distinct ligand specificities (Mohammadi M, Olsen S K and Ibrahimi O A. (2005), *Cytokine Growth Factor Rev* 16: 107-137, Ornitz D M and Itoh N. (2001). *Genome Biol* 2: REVIEWS3005). For FGFR2, cells of an epithelial linage only express the "IIIb" isoform encoded by exon 8 (FGFR2b; SEQ ID NO:2; NP_07529.2), while mesenchymally derived cells only express the "IIIc" isoform utilizing exon 9 (FGFR2c; SEQ ID NO:3; NP_000132.1) (Scotet E and Houssaint E. (1995). *Biochim Biophys Acta* 1264: 238-242). The FGFR2b iosform predominantly binds FGF1, FGF3, FGF7 and FGF10, while FGFR2c does not bind FGF7 and FGF10 but does bind FGF1, FGF2, FGF4, FGF6, and FGF8 with high affinity (Ibrahimi O A, Zhang F, Eliseenkova A V, Itoh N, Linhardt R J and Mohammadi M. (2004), *Hum Mol Genet* 13: 2313-2324).

An "increased activity" or "activation mutation" of FGFR2 in a test subject or a biological sample refers to higher total FGFR2 activity in the test subject or biological sample in comparison with a control, e.g., a healthy subject or a standard sample. Preferably, although not necessarily, the activity is at least 10%, more preferably at least 50%, even more preferably at least 100%, and still more preferably at least 150% higher in the test subject or sample than in the control. The increased activity, for example, may result from increased basal FGFR2 activity, prolonged stimulation, delayed degradation, or over-expression, e.g., due to enhanced ligand binding, promiscuous or inappropriate ligand binding, constitutive receptor dimerization, impaired recycling resulting in augmentation of signaling, delayed degradation, or kinase activation.

A higher expression level of FGFR2 may result from, for example, a mutation in a non-coding region of a FGFR2 gene or a mutation in a coding or non-coding gene involved in FGFR2 transcription or translation. The expression level of FGFR2 can be determined, for example, by comparing FGFR2 mRNA or the level of FGFR2 protein in a test subject as compared to a control, for example by comparing the tumor to normal endometrium (e.g., a normal adjacent endometrium sample).

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide.

Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "variant" also includes a polypeptide or enzyme which has at least 60% amino acid identity as determined by BLAST or FASTA algorithms, preferably at least 75% most preferably at least 85%, and even more preferably at least 90%, and still more preferably at least 95%, and which has the same or substantially similar properties or functions as the native or parent protein or enzyme to which it is compared. A particular variant is a "gain-of-function" variant, meaning a polypeptide variant in which the change of at least one given amino acid residue in a protein or enzyme improves a specific function of the polypeptide, including, but not limited to protein activity. The change in amino acid residue can be replacement of an amino acid with one having similar properties.

As used herein, the terms "homologous" and "similar" refer to the relationship between proteins that possess a "common evolutionary origin," including proteins from superfamilies (e.g., the immunoglobulin superfamily) and homologous proteins from different species. Such proteins (and their encoding genes) have sequence homology, as reflected by their sequence similarity, whether in terms of percent similarity or the presence of specific residues or motifs as conserved positions.

In a specific embodiment, two DNA sequences are "substantially homologous or similar" when at least about 80%, and most preferably at least about 90% or at least 95%) of the nucleotides match over the defined lengths of the DNA sequences, as determined by sequence comparison algorithms, such as, BLAST, FASTA, DNA Strider, etc.

The terms "mutant" and "mutation" mean any detectable change in genetic material, e.g., DNA, or any process mechanism, or result of such a change. When compared to a control material, such change may be referred to as an "abnormality." This includes gene mutations, in which the structure (e.g. DNA sequence of a gene is altered, any gene or DNA arising from any mutation process, and any expression product (e.g., protein) expressed by a modified gene or DNA sequence. The term "variant" may also be used to indicate a modified or altered gene, DNA sequence, enzyme, cell, etc., i.e., any kind of mutant.

As used herein, "sequence-specific oligonucleotides" refers to related sets of oligonucleotides that can be used to detect specific variations or mutations in the FGFR2 gene, preferably a FGFR2 activation mutation.

A "probe" refers to a nucleic acid or oliognucleotide that forms a hybrid structure with a sequence in a target region due to complementarity of at least one sequence in the probe with a sequence in the target protein of the subject.

The present invention provides antisense nucleic acids (including ribozymes), which may be used to inhibit expression of FGFR2. An "antisense nucleic acid" is preferably a single stranded nucleic acid molecule which, on hybridizing under cytoplasmic conditions with complementary bases in an RNA or DNA molecule, inhibits the latter's role. If the RNA is messenger RNA transcript, the antisense nucleic acid is a countertranscript or mRNA-interfering complementary nucleic acid. As presently used, "antisense" broadly includes RNA-RNA interactions, RNA-DNA interactions, ribozymes, RNA-induced silencing complexes, and RNASe-H mediated arrest. Antisense nucleic acid molecules can be encoded by a recombinant gene for expression in a cell (e.g., U.S. Pat. No. 5,814,500; U.S. Pat. No. 5,811,234), or alternatively they can be prepared synthetically (e.g., U.S. Pat. No. 5,780,607). Synthetic oligonucleotides are suitable for antisense use.

Diagnostic Methods

According to the present invention, mutations of the FGFR2 receptor that induce receptor activation, which includes overexpression and delayed degradation, can be detected to diagnose or classify endometrial cancer or precancer in a subject.

As used herein, a "subject" is a human or non-human mammal, e.g., a primate, cow, horse, pig, sheep, goat, dog, cat, or rodent, likely to develop endometrial cancer. In all embodiments human subjects are preferred. Preferably the subject is a human either suspected of having endometrial cancer, having been diagnosed with endometrial cancer, or having a family history of endometrial cancer. Methods for identifying subjects suspected of having endometrial cancer may include physical examination, subject's family medical history, subject's medical history, endometrial biopsy, or a number of imaging technologies such as ultrasonography, computed tomography, magnetic resonance imaging, magnetic resonance spectroscopy, or positron emission tomography. Diagnostic method for endometrial cancer and the clinical delineation of endometrial cancer diagnoses are well known to those of skill in the medical arts.

Accordingly, diagnostic methods may comprise for example, detecting a mutation in the FGFR2 gene, wherein the mutation results in increased FGFR2 receptor activity. The FGFR2 mutation may especially affect a coding region of the FGFR2 gene, such as, for example, a mutation in the IgII or IgIII domain of the FGFR2 gene. The mutation may be a missense mutation, preferably a missense mutation resulting in nucleic acid substitution, or a deletion, or a combination of both. Preferably, the mutation results in one, and sometimes more, amino acid substitutions or deletions, e.g., see Table 2 below.

The diagnostic methods of the invention also encompass detecting a mutation in the FGFR2 protein, in particular a mutation that results in increased activity of the FGFR2 protein. Preferably the mutation is at least one mutation in FGFR2 selected from the group consisting of: a mutation in the junction between the immunoglobulin-like (Ig) domains II and III; a mutation in the IgIII domain; a mutation in the junction between the IgIII domain and the transmembrane (TM) domain; a mutation in the TM domain; a mutation in the junction between the TM domain and the tyrosine kinase domain I; a mutation in the tyrosine kinase domain I, or a mutation in the tyrosine kinase domain II. Most preferably the mutation induces an amino acid substitution in FGFR2, for example, a S to W mutation at position 252 of SEQ ID NOS:2 or 3, or N to K mutation at position 550 of SEQ ID NO:2 or position 549 of SEQ ID NO:3. In another embodiment, the amino acid substitution in FGFR2 is a K to R mutation at position 310 of SEQ ID NOS:2 or 3; or a M to R mutation at position 392 of SEQ ID NO:2 or position 391 of SEQ ID NO:3. In one nonlimiting embodiment, the mutation is consist of a deletion of nucleotide C and T at position 2290-91 of SEQ ID NO:1 (NM-02297.2); SEQ ID NO:7; or an IVS10+2A>C splicing mutation.

Typically, a detected FGFR2 receptor activation mutation increases activation of the receptor by, for example, enhancing ligand binding, altered (promiscuous) ligand affinity, constitutive receptor dimerization, delayed degradation, impaired recycling from the cell membrane, overexpression, or kinase activation, thereby activating the FGFR2 receptor.

As used herein, the term "diagnosis" refers to the identification of the disease at any stage of its development, and also includes the determination of a predisposition of a subject to develop the disease or relapse. The invention further provides a means of confirming and classifying the type of endometrial cancer.

The term "biological sample" refers to any cell source from which DNA may be obtained. Preferably the biological sample are obtained from the uterus area or near thereto to ensure that endometrial cells lining the uterus are present in the biological sample. In one embodiment the biological sample is in the form of blood, for example, uterine blood from menstrual or post menopausal spotting.

In a further embodiment, the diagnosis of endometrial cancer in a subject comprises assessing the level of expression, delayed degradation, or activity of the FGFR2 protein in endometrial cells of a test subject and comparing it to the level of expression or activity in endometrial cells of a control subject, wherein an increased expression and/or activity of FGFR2 protein in the test subject compared to the control subject is indicative of endometrial cancer or precancer.

The level of expression or delayed degradation of FGFR2 may be assessed by determining the amount of mRNA that encodes the FGFR2 protein in a biological sample, or by determining the concentration of FGFR2 protein in a biological sample. The level of FGFR2 activity may be assessed by determining the level of activity in a FGFR2 signaling pathway signaling flux, e.g., by measuring FGFR2 activity in a sample or subject, as described herein.

Nucleic Acid Based Assays

According to the invention, mutated forms of FGFR2 nucleic acids, i.e. in the FGFR2 DNA or in its transcripts, as well as a deregulated expression, e.g. overexpression, of FGFR2 or other components of a FGFR2 pathway can be detected by a variety of suitable methods.

Standard methods for analyzing and sequencing the nucleic acid contained in a biological sample and for diagnosing a genetic disorder can be employed, and many strategies for genotypic analysis are known to those of skilled in the art.

In a preferred embodiment, the determination of mutations in the FGFR2 gene encompasses the use of nucleic acid sequences such as specific oligonucleotides, to detect mutations in FGFR2 genomic DNA or mRNA in a biological sample. Such oligonucleotides may be specifically hybridize to a site of mutation, or to a region adjacent to this site of mutation present in a FGFR2 nucleic acid. One may also employ primers that permit amplification of all or part of FGFR2. Alternatively, or in combination with such techniques, oligonucleotide sequencing described herein or known to the skilled artisan can be applied to detect the FGFR2 mutations.

One skilled in the art may use hybridization probes in solution and in embodiments employing solid-phase procedures. In embodiments involving solid-phase procedures, the test nucleic acid is adsorbed or otherwise affixed to a selected matrix or surface. The fixed, single-stranded nucleic acid is then subjected to specific hybridization with selected probes.

In another embodiment, one skilled in the art may use oligonucleotide primers in an amplification technique, such as PCR or reverse-PCR ("reverse polymerase chain reaction"), to specifically amplify the target DNA or mRNA, respectively, which is potentially present in the biological sample.

Useful oligonucleotides include primers that permit amplification of FGFR2 exons.

The present invention is more particularly directed to a method of in vitro diagnosis of endometrial cancer or precancer comprising the steps of:

a) contacting a biological sample containing DNA with specific oligonucleotides permitting the amplification of all or part of the FGFR2 gene, the DNA contained in the sample having being rendered accessible, where appropriate, to hybridization, and under conditions permitting a hybridization of the primers with the DNA contained in the biological sample;

b) amplifying said DNA;

c) detecting the amplification products;

d) comparing the amplified products as obtained to the amplified products obtained with a normal control biological sample, and thereby detecting a possible abnormality in the FGFR2 gene.

In certain embodiments, the DNA a biological sample is sequenced directly with no requirement for amplification. In these embodiments, the sequenced DNA is compared to a control sequence for detecting possible abnormalities in the FGFR2 gene.

The method of the invention can also be applied to the detection of an abnormality in the transcript of the FGFR2 gene, e.g., by amplifying the mRNAs contained in a biological sample, for example by RT-PCR.

Thus another subject of the present invention is a method of in vitro diagnosis of endometrial cancer, as previously defined comprising the steps of:

a) producing cDNA from mRNA contained in a biological sample;

b) contacting said cDNA with specific oligonucleotides permitting the amplification of all or part of the transcript of the FGFR2 gene, under conditions permitting a hybridization of the primers with said cDNA;

c) amplifying said cDNA;

d) detecting the amplification products;

e) comparing the amplified products as obtained to the amplified products obtained with a normal control biological sample, and thereby detecting a possible abnormality in the transcript of the FGFR2 gene.

A control can be any normal endometrial control sample known to those skilled in the art, for example, a normal adjacent endometrium sample or a normal DNA, obtained from blood or buccal swab.

For RNA analysis, the biological sample may be any cell source, as described above, such as a biopsy tissue, from which RNA is isolated using standard methods well known to those of ordinary skill in the art such as guanidium thiocyanate-phenol-chloroform extraction (Chomocyznski et al., Anal. Biochem., 1987, 162:156). The isolated RNA is then subjected to coupled reverse transcription and amplification by polymerase chain reaction (RT-PCR), using specific oligonucleotide primers that are specific for a selected site. Conditions for primer annealing are chosen to ensure specific reverse transcription and amplification; thus, the appearance of an amplification product is diagnostic of the presence of a particular genetic variation. In another embodiment, RNA is reverse-transcribed and amplified, after which the amplified sequences are identified by, e.g., direct sequencing. In still another embodiment, cDNA obtained from the RNA can be cloned and sequenced to identify a mutation.

The FGFR2 nucleic acids of the invention can also be used as probes, e.g., in therapeutic and diagnostic assays. For instance, the present invention provides a probe comprising a substantially purified oligonucleotide, which oligonucleotide comprises a region having a nucleotide sequence that is capable of hybridizing specifically to a region of a FGFR2 gene which differs from that of the wild-type gene (SEQ ID NOS:1 and 7), e.g., a mutant or polymorphic region. Such probes can then be used to specifically detect which mutation of the FGFR2 gene is present in a sample taken from a subject. The mutant or polymorphic region can be located in the promoter, exon, or intron sequences of the FGFR2 gene.

Particularly preferred probes of the invention have a number of nucleotides sufficient to allow specific hybridization to the target nucleotide sequence. Thus, probes of suitable lengths based on SEQ ID NOS:1-3 and complementary to the mutant sequences provided herein can be constructed and tested by the skilled artisan for appropriate level of specificity depending on the application intended. Where the target nucleotide sequence is present in a large fragment of DNA, such as a genomic DNA fragment of several tens or hundreds of kilobases, the size of the probe may have to be longer to provide sufficiently specific hybridization, as compared to a probe which is used to detect a target sequence which is present in a shorter fragment of DNA. For example, in some diagnostic methods, a portion of the FGFR2 gene may first be amplified and thus isolated from the rest of the chromosomal DNA and then hybridized to a probe. In such a situation, a shorter probe will likely provide sufficient specificity of hybridization. For example, a probe having a nucleotide sequence of about 10 nucleotides may be sufficient, although probes of about 15 nucleotides, even more preferably 20 nucleotides, are preferred.

In a preferred embodiment, the probe or primer further comprises a label attached thereto, which preferably is capable of being detected. The label can, for example, be selected from radioisotopes, fluorescent compounds, enzymes, and enzyme co-factors.

In another preferred embodiment of the invention, the isolated nucleic acid, which is used, e.g., as a probe or a primer, is modified, such as to become more stable. Exemplary nucleic acid molecules which are modified include phosphoramidate, phosphothioate and methylphosphonate analogs of DNA (see also U.S. Pat. Nos. 5,176,996; 5,264, 564; and 5,256,775).

In yet another embodiment, one may use HPLC or denaturing HPLC (DHPLC) techniques to analyze the FGFR2 nucleic acids. DHPLC was developed when observing that, when HPLC analyses are carried out at a partially denaturing temperature, i.e., a temperature sufficient to denature a heteroduplex at the site of base pair mismatch, homoduplexes can be separated from heteroduplexes having the same base pair length (Hayward-Lester, et al., Genome Research, 1995, 5:494; Underhill, et al., Proc. Natl. Acad. Sci. USA, 1996, 93:193; Doris, et al., DHPLC Workshop, 1997, Stanford University). Thus, the use of DHPLC was applied to mutation detection (Underhill, et al., Genome Research, 1997, 7:996; Liu, et al., Nucleic Acid Res., 1998, 26; 1396). DHPLC can separate heteroduplexes that differ by as little as one base pair. "Matched Ion Polynucleotide Chromatography" (MIPC), or Denaturing "Matched Ion Polynucleotide Chromatography" (DMIPC) as described in U.S. Pat. No. 6,287,822 or 6,024,878, are separation methods that can also be useful in connection with the present invention.

Alternatively, one can use the DGGE method (Denaturing Gradient Gel Electrophoresis), or the SSCP method (Single Strand Conformation Polymorphism) for detecting an abnormality in the FGFR2 gene. DGGE is a method for resolving two DNA fragments of identical length on the basis of sequence differences as small as a single base pair change, using electrophoresis through a gel containing varying concentrations of denaturant (Guldberg et al., Nuc. Acids Res. 1994, 22:880). SSCP is a method for detecting sequence differences between two DNAs, comprising hybridization of the two species with subsequent mismatch detection by gel electrophoresis (Ravnik-Glavac et al., Hum. Mol. Genet. 1994, 3:801). "HOT cleavage", a method for detecting sequence differences between two DNAs, comprising hybridization of the two species with subsequent mismatch detection by chemical cleavage (Cotton, et al., Proc. Natl. Acad. Sci. USA 1988, 85:4397), can also be used. Such methods are preferably followed by direct sequencing. Advantageously, the RT-PCR method may be used for detecting abnormalities in the FGFR2 transcript, as it allows to visualize the consequences of a splicing mutation such as exon skipping or aberrant splicing due to the activation of a cryptic site. Preferably this method is followed by direct sequencing as well.

Techniques using microarrays, preferably microarray techniques allowing for high-throughput screening, can also be advantageously implemented for detecting an abnormality in the FGFR2 gene or for assaying expression of the FGFR2 gene or the gene of another component in the FGFR2 pathway resulting in increased signaling as described herein. Microarrays may be designed so that the same set of identical oligonucleotides is attached to at least two selected discrete regions of the array, so that one can easily compare a normal sample, contacted with one of said selected regions of the array, against a test sample, contacted with another of said selected regions. These arrays avoid the mixture of normal sample and test sample, using microfluidic conduits. Useful microarray techniques include those developed by Nanogen, Inc (San Diego, Calif.) and those developed by Affymetrix. However, all types of microarrays, also called "gene chips" or "DNA chips", may be adapted for the identification of mutations. Such microarrays are well known in the art.

The solid support on which oligonucleotides are attached may be made from glass, silicon, plastic (e.g., polypropylene, nylon), polyacrylamide, nitrocellulose, or other materials. One method for attaching the nucleic acids to a surface is by printing on glass plates, as is described generally by Schena et al., Science 1995, 270:467-470. This method is especially useful for preparing microarrays of cDNA. See also DeRisi et al., Nature Genetics 1996, 14:457-460; Shalon et al., Genome Res. 1996, 6:639-645; and Schena et al., Proc. Natl. Acad. Sci. USA 1995, 93:10539-11286.

Other methods for making microarrays, e.g., by masking (Maskos and Southern, Nuc. Acids Res. 1992, 20:1679-1684), may also be used. In principal, any type of array, for example, dot blots on a nylon hybridization membrane (see Sambrook et al., Molecular Cloning A Laboratory Manual (2nd Ed.), Vol. 1-3, Cold Spring Harbor Laboratory, Cold Spring Harbor, N.Y., 1989) could be used, although, as will be recognized by those of skill in the art, very small arrays will be preferred because hybridization volumes will be smaller. For these assays nucleic acid hybridization and wash conditions are chosen so that the attached oligonucleotides "specifically bind" or "specifically hybridize" to at least a portion of the FGFR2 gene present in the tested sample, i.e., the probe hybridizes, duplexes or binds to the FGFR2 locus with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls (see, e.g., Shalon et al., supra, and Chee et al., Science 1996, 274:610-614).

A variety of methods are available for detection and analysis of the hybridization events. Depending on the reporter group (fluorophore, enzyme, radioisotope, etc.) used to label the DNA probe, detection and analysis are carried out fluorimetrically, colorimetrically or by autoradiography. By observing and measuring emitted radiation, such as fluorescent radiation or a particle emission, information may be obtained about the hybridization events.

When fluorescently labeled probes are used, the fluorescence emissions at each site of transcript array can, preferably be detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al. Genome Res. 1996, 6:639-695).

Protein Based Assays

As an alternative to analyzing FGFR2 nucleic acids, one can evaluate FGFR2 on the basis of mutations in the protein, or dysregulated production, e.g., overproduction, of the protein.

In preferred embodiments, FGFR2 are detected by immunoassay. For example, Western blotting permits detection of a specific variant, or the presence or absence of FGFR2. In particular, an immunoassay can detect a specific (wild-type or mutant) amino acid sequence in a FGFR2 protein. Other immunoassay formats can also be used in place of Western blotting, as described below for the production of antibodies. One of these is ELISA assay.

In ELISA assays, an antibody against FGFR2, an epitopic fragment of FGFR2, is immobilized onto a selected surface, for example, a surface capable of binding proteins such as the wells of a polystyrene microtiter plate. After washing to remove incompletely adsorbed polypeptides, a nonspecific protein such as a solution of bovine serum albumin (BSA) may be bound to the selected surface. This allows for blocking of nonspecific adsorption sites on the immobilizing surface and thus reduces the background caused by nonspecific bindings of antisera onto the surface. The immobilizing surface is then contacted with a sample, to be tested in a manner conductive to immune complex (antigen/antibody) formation. This may include diluting the sample with diluents, such as solutions of BSA, bovine gamma globulin (BGG) and/or phosphate buffered saline (PBS)/Tween®. The sample is then allowed to incubate for from 2 to 4 hours, at temperatures between about 25 to 37 degrees C. Following incubation, the sample-contacted surface is washed to remove non-immunocomplexed material. The washing procedure may include washing with a solution, such as PBS/ Tween® or borate buffer. Following formation of specific immunocomplexes between the test sample and the bound antibody, and subsequent washing, the occurrence, and an even amount of immunocomplex formation may be determined by subjecting the immunocomplex to a second antibody against FGFR2 mutants, that recognizes a mutated epitope on the protein. To provide detecting means, the second antibody may have an associated activity such as an enzymatic activity that will generate, for example, a color development upon incubating with an appropriate chromogenic substrate. Quantification may then be achieved by measuring the degree of color generation using, for example, a visible spectra spectrophotometer.

Typically the detection antibody is conjugated to an enzyme such as peroxidase and the protein is detected by the addition of a soluble chromophore peroxidase substrate such as tetramethylbenzidine followed by 1 M sulfuric acid. The test protein concentration is determined by comparison with standard curves.

These protocols are detailed in Current Protocols in Molecular Biology, V. 2 Ch. 11 and Antibodies, a Laboratory Manual, Ed Harlow, David Lane, Cold Spring Harbor Laboratory (1988) pp 579-593.

Alternatively, a biochemical assay can be used to detect expression, or accumulation of FGFR2, e.g., by detecting the presence or absence of a band in samples analyzed by polyacrylamide gel electrophoresis; by the presence or absence of a chromatographic peak in samples analyzed by any of the various methods of high performance liquid chromatography, including reverse phase, ion exchange, and gel permeation; by the presence or absence of FGFR2 in analytical capillary electrophoresis chromatography, or any other quantitative or qualitative biochemical technique known in the art.

The immunoassays discussed above involve using antibodies directed against the FGFR2 protein or fragments thereof. The production of such antibodies is described below.

Anti-FGFR2 Antibodies

Such antibodies include but are not limited to polyclonal, monoclonal, chimeric, single chain, Fab fragments, Fab expression library, and for example, humanized antibodies.

Various procedures known in the art may be used for the production of polyclonal or monoclonal antibodies to FGFR2 polypeptides or derivative or analog thereof. For the production of antibody, various host animals can be immunized by injection with the antigenic polypeptide, including but not limited to rabbits, mice, rats, sheep, goats, etc.

For preparation of monoclonal antibodies directed toward the FGFR2 polypeptides, any technique that provides for the production of antibody molecules by continuous cell lines in culture may be used. These include but are not limited to the hybridoma technique originally developed by Kohler and Milstein (Nature 256:495-497, 1975), as well as the trioma technique, the human B-cell hybridoma technique (Kozbor et al., Immunology Today 4:72, 1983; Cote et al., Proc. Natl. Acad. Sci. U.S.A. 80:2026-2030, 1983), and the EBV-hybridoma technique to produce human monoclonal antibodies (Cole et al., in Monoclonal Antibodies and Cancer Therapy, Alan R. Liss, Inc., pp. 77-96, 1985). In an additional embodiment of the invention, monoclonal antibodies can be produced in germ-free animals (International Patent Publication No. WO 89/12690, published Dec. 28, 1989). According to the invention, techniques described for the production of single chain antibodies (U.S. Pat. Nos. 5,476, 786 and 5,132,405 to Huston; U.S. Pat. No. 4,946,778) can be adapted to produce the FGFR2 polypeptide-specific single chain antibodies. Indeed, these genes can be delivered for expression in vivo. An additional embodiment of the invention utilizes the techniques described for the construction of Fab expression libraries (Huse et al., Science 246: 1275-1281, 1989) to allow rapid and easy identification of monoclonal Fab fragments with the desired specificity for a FGFR2 polypeptide, or its derivatives, or analogs.

Antibody fragments which contain the idiotype of the antibody molecule can be generated by known techniques. For example, such fragments include but are not limited to: the F(ab').sub.2 fragment which can be produced by pepsin digestion of the antibody molecule; the Fab' fragments which can be generated by reducing the disulfide bridges of the F(ab').sub.2 fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

Diagnositc Kits

The present invention further provides kits for the determination of the sequence within the FGFR2 gene in a subject to diagnose or classify endometrial cancer. The kits comprise a means for determining the sequence at the variant positions, and may optionally include data for analysis of mutations. The means for sequence determination may comprise suitable nucleic acid-based and immunological reagents. Preferably, the kits also comprise suitable buffers, control reagents where appropriate, and directions for determining the sequence at a variant position and for diagnosing or classifying endometrial cancer in a subject.

Nucleic Acid Based Diagnostic Kits

The invention provides nucleic acid-based methods for detecting genetic variations of FGFR2 in a biological sample. The sequence at particular positions in the FGFR2 gene is determined using any suitable means known in the art, including without limitation one or more of hybridization with specific probes for PCR amplification, restriction fragmentation, direct sequencing, SSCP, and other techniques known in the art.

In one embodiment, diagnostic kits include the following components:

a) Probe DNA: The probe DNA may be pre-labeled; alternatively, the probe DNA may be unlabeled and the ingredients for labeling may be included in the kit in separate containers; and b) Hybridization reagents: The kit may also contain other suitably packaged reagents and materials needed for the particular hybridization protocol, including solid-phase matrices, if applicable, and standards.

In another embodiment, diagnostic kits include:

a) Sequence determination primers: Sequencing primers may be pre-labeled or may contain an affinity purification or attachment moiety; and b) Sequence determination reagents: The kit may also contain other suitably packaged reagents and materials needed for the particular sequencing protocol.

In one preferred embodiment, the kit comprises a panel of sequencing primers, whose sequences correspond to sequences adjacent to variant positions.

Antibody Based Diagnostic Kits

The invention also provides antibody-based methods for detecting mutant (or wild type) FGFR2 proteins in a biological sample. The methods comprise the steps of: (i) contacting a sample with one or more antibody preparations, wherein each of the antibody preparations is specific for mutant (or wild type) FGFR2 under conditions in which a stable antigen-antibody complex can form between the antibody and FGFR2 in the biological sample; and (ii) detecting any antigen-antibody complex formed in step (i) using any suitable means known in the art, wherein the detection of a complex indicates the presence of mutant (or wild type) FGFR2.

Typically, immunoassays use either a labeled antibody or a labeled antigenic component (e.g., that competes with the antigen in the sample for binding to the antibody). Suitable labels include without limitation enzyme-based, fluorescent, chemiluminescent, radioactive, or dye molecules. Assays that amplify the signals from the probe are also known, such as, for example, those that utilize biotin and avidin, and enzyme-labeled immunoassays, such as ELISA assays.

Diagnostic kits typically include one or more of the following components:

(i) FGFR2-specific antibodies: The antibodies may be pre-labeled; alternatively, the antibody may be unlabeled and the ingredients for labeling may be included in the kit in separate containers, or a secondary, labeled antibody is provided; and (ii) Reaction components: The kit may also contain other suitably packaged reagents and materials needed for the particular immunoassay protocol, including solid-phase matrices, if applicable, and standards.

The kits referred to above preferably includes instructions for conducting and reading the test to diagnose or classify endometrial cancer. Furthermore, in preferred embodiments, the diagnostic kits are adaptable to high-throughput and/or automated operation.

Methods of Treating Endometrial Cancer

The present invention further provides a method of treating endometrial cancer characterized by FGFR2 activation. The treatment method preferably comprises inhibition of the FGFR2 activity in a subject. Generally the method comprises administering to a patient in need of such treatment an effective amount of an agent that modulates FGFR2 expression or activity, with a pharmaceutically acceptable carrier. For example, the therapeutic agent may be a FGFR2 antisense nucleic acid, an anti-FGFR2 intracellular inhibitory antibody or a small molecule inhibitor.

The treatment compositions comprise, as active principle agents a FGFR2 inhibitor. Examples of suitable inhibitors includes those inhibitors that inhibit FGFR2 DNA synthesis and its expression products (e.g., FGFR2 RNA or protein). In one exemplary embodiment the inhibitor is a small molecule FGFR2 inhibitor, e.g., PD173074. In another exemplary embodiment RNA interference is used, wherein the inhibitor is a reagent that inhibits RNA synthesis and/or translation, e.g., a small inhibitory RNA (siRNA), a small hairpin RNA (shRNA), microRNA (miRNA), or a ribozyme.

In yet another embodiment the inhibitor comprises antibodies directed against FGFR2, preferably a mutated FGFR2, and particularly against at least one Ig domain thereof. Preferably the antibodies are specific for a mutated linker region between IgII and IgIII domains of FGFR2, e.g., against the S252W mutation. Generally, preferred antibodies are monoclonal ones, and particularly antibodies modified so that they do not induce immunogenic reactions in a human subject (e.g., humanized antibodies). Antibodies that block the activity of FGFR2 may be produced and selected according to any standard method well-known by one skilled in the art, such as those described above in the context of diagnostic applications.

Intracellular antibodies (sometime referred to as "intrabodies") have been used to regulate the activity of intracellular proteins in a number of systems (see, Marasco, Gene Ther. 1997, 4:11; Chen et al., Hum. Gene Ther. 1994, 5:595), e.g., viral infections (Marasco et al., Hum. Gene Ther. 1998, 9:1627) and other infectious diseases (Rondon et al., Annu. Rev. Microbiol. 1997, 51:257), and oncogenes, such as p21 (Cardinale et al., FEBS Lett. 1998, 439:197-202; Cochet et al., Cancer Res. 1998, 58:1170-6), myb (Kasono et al., Biochem Biophys Res Commun. 1998, 251:124-30), erbB-2 (Graus-Porta et al., Mol Cell Biol. 1995, 15:1182-91), etc. This technology can be adapted to inhibit FGFR2 activity by expression of an anti-FGFR2 intracellular antibody.

Other inhibitors that would be suitable include antisense oligonucleotides directed against FGFR2, more preferably a mutated FGFR2 isoform. Vectors comprising a sequence encoding an antisense nucleic acid according to the invention may be administered by any known methods, such as the methods for gene therapy available in the art. For general reviews of the methods of gene therapy, see, Goldspiel et al., Clinical Pharmacy 1993, 12:488-505; Wu and Wu, Biotherapy 1991, 3:87-95; Tolstoshev, Ann. Rev. Pharmacol. Toxicol. 1993, 32:573-596; Mulligan, Science 1993, 260: 926-932; and Morgan and Anderson, Ann. Rev. Biochem. 1993, 62:191-217; May, TIBTECH 1993, 11:155-215. Methods commonly known in the art of recombinant DNA technology that can be used are described in Ausubel et al., (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al., (eds.), 1994, Current Protocols in Human Genetics, John Wiley & Sons, NY.

The term "treatment" as used herein is to therapeutically intervene in the development or progression of a endometrial cancer in a subject. The term "treatment" also encompasses prevention of the development or reoccurence of endometrial cancer in a subject diagnosed as having a known FGFR2 activation mutation.

The term "therapeutically effective amount" is used herein to mean an amount or dose sufficient to modulate, e.g., decrease the level of FGFR2 activity e.g., by about 10 percent, preferably by about 50 percent, and more preferably by about 90 percent. Preferably, a therapeutically effective amount can ameliorate or present a clinically significant deficit in the activity, function and response of the subject. Alternatively, a therapeutically effective amount is sufficient to cause an improvement in a clinically significant condition in the subject.

The FGFR2 inhibitor inhibits FGFR2 activity or expression and is advantageously formulated in a pharmaceutical composition, with a pharmaceutically acceptable carrier.

This substance may be then called an active ingredient or a therapeutic agent against endometrial cancer.

The concentration or amount of the active ingredient depends on the desired dosage and administration regimen, as discussed below. Suitable dose ranges largely depend on the FGFR2 inhibitor used, but may include, for purposes of exemplifying only, from about 0.01 mg/kg to about 100 mg/kg of body weight per day.

The pharmaceutical compositions may also include other biologically active compounds. The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

According to the invention, the pharmaceutical composition of the invention can be introduced parenterally, transmucosally, e.g., orally (per os), nasally, vaginally, or rectally, or transdermally. Parental routes include intravenous, intra-arteriole, intramuscular, intradermal, subcutaneous, intraperitoneal, intraventricular, and intracranial administration. Targeting the uterus directly, e.g. by direct administration to uterus or uterus lining, may be advantageous.

In one embodiment, the therapeutic compound can be delivered in a controlled release system. For example, a polypeptide may be administered using intravenous infusion with a continuous pump, in a polymer matrix such as polylactic/glutamic acid (PLGA), a pellet containing a mixture of cholesterol and the active ingredient (SilasticR™; Dow Corning, Midland, Mich.; see U.S. Pat. No. 5,554,601) implanted subcutaneously, an implantable osmotic pump, a transdermal patch, liposomes, or other modes of administration.

Examples of the invention are provided, and are understood to be exemplary only, and do not limit the scope of the invention or the appended claims. A person of ordinary skill in the art will appreciate the invention can be practiced in any forms according to the claims and disclosure here.

EXAMPLE 1

Detection of Activating FGFR2 Mutations in Endometrial Cancer

Our findings show that activation and overexpression of FGFR2 plays a role in endometrial tumorigenesis. Exon 8 is three nucleotides longer than exon 9, hence the FGFR2b isoform is one codon longer than the FGFR2c isoform. Specificity of signaling is also provided by tissue specific expression of receptors, ligands and heparin sulphate proteoglycans (Allen et al., 2001; Fiore, 2001). Due to the differences in length of the FGFR2 "b" and "c" isoforms, all mutations will be numbered relative to the epithelially expressed FGFR2b isoform (SEQ ID NO:2; NP_075259.2). For those occurring downstream of exon 8 we provide herein the equivalent mutation numbered relative to the FGFR2c isoform (SEQ ID NO:3; NP_000132.1) in brackets and in Table 2. The N550K (N549K) variant identified in two of the endometrial cell lines was likely to result in receptor activation as identical or similar germline missense changes had been reported in FGFR2 and FGFR3 in patients with Crouzon syndrome (Kan et al., 2002) and hypochondroplasia (Bellus et al., 1995) (FIG. 1).

Next we sought to determine the spectrum and frequency of activating FGFR2 mutations in primary uterine cancers. Direct sequencing of the exons in which activating mutations in FGFR2 and FGFR3 had previously been identified in the germline (exons 7, 8, 10, 13 and 15) was performed for 187 primary uterine cancers, representing all grades and stages of tumors and the major histologic subtypes of endometrial carcinoma (Table 1).

TABLE 1

Uterine cancer patient demographics, disease characteristics and FGFR2 mutation status

| | Cohort n = 187 | |
|---|---|---|
| | Entire Uterine Cancer Cohort n (%) | Cases with FGFR2 mutations n (%) |
| Age (years) | 66.5 ± 11.1* | |
| Race | | |
| Caucasian | 150 (80) | 18 (12) |
| African American | 33 (18) | 1 (3) |
| Other or not specified | 4 (2) | 0 (0) |
| Histology | | |
| Endometrioid | 115 (61) | 18 (16) |
| Serous or mixed serous/endometrioid | 45 (24) | 1 (2) |
| Clear cell | 8 (4) | 0 (0) |
| Adenocarcinoma not otherwise specified | 1 (<1) | 0 (0) |
| Carcinosarcoma | 17 (9) | 0 (0) |
| Uterine stromal sarcoma | 1 (<1) | 0 (0) |
| Stage | | |
| I | 79 (42) | 9 (11) |
| II | 16 (9) | 1 (6) |
| III | 67 (36) | 6 (9) |
| IV | 25 (13) | 3 (12) |
| FIGO Grade | | |
| 1 | 49 (26) | 7 (14) |
| 2 | 39 (21) | 9 (23) |
| 3† | 99 (53) | 3 (3) |

*Mean ± standard deviation
†All carcinomas with serous and clear cell features along with carcinosarcomas and sarcoma classified as grade 3

It should be noted that the A315T reported in ESS-1 derived from an endometrial stromal sarcoma occurred in the mesenchymally expressed isoform (FGFR2c) and all carcinosarcomas (tumors with both malignant epithelial and stromal elements) were also screened for mutations in exon 9 (NM_000141). For a subset of tumors (32 endometrioid endometrial cancers plus 17 carcinosarcomas) exons 5-18 encompassing the second and third immunoglobulin domains (hereafter referred to as D2 and D3), transmembrane domain and the entire kinase domain were sequenced to determine the relative occurrence of novel somatic mutations. In addition to the mutations found in exons 7, 10, 13 and 15, one additional mutation was identified in this more extensive mutational screen, a 2 bp deletion in exon 18.

Mutations were identified in 19 cases (10%). Eighteen of 115 endometrioid endometrial cancers (16%) had mutations and a single serous carcinoma (1 of 45, 2%) harbored a mutation. No mutations were seen in carcinosarcomas or clear cell cancers.

mutations are summarized in Table 2. The S252W mutation was the most common mutation identified, seen in 8 independent tumors. This mutation occurs in the linker region between D2 and D3, which provides key contacts with the FGF ligand. The S252W and the adjacent P253R mutations

TABLE 2

Spectrum of FGFR2 mutations in primary endometrial cancers.

| Case ID | FGFR2b Nucleotide[a] | FGFR2b Codon[b] | FGFR2c Codon[c] | Histotype | Stage | Grade | MSI status |
|---|---|---|---|---|---|---|---|
| AN3 CA[d] | A929G | K310R | K310R | endometrioid | | | positive |
| AN3 CA[d] | T1650G | N550K | N549K | endometrioid | | | positive |
| MFE296 | T1650G | N550K | N549K | endometrioid | | | negative |
| ESS-1 | G943A[e] | | A315T[f] | Stromal sarcoma | | | negative |
| 1359 | C755G | S252W | S252W | endometrioid | I | 2 | positive |
| 1574 | C755G | S252W | S252W | endometrioid | I | 2 | positive |
| 1492[d] | C755G | S252W | S252W | endometrioid | I | 1 | negative |
| 1484 | C755G | S252W | S252W | endometrioid | III | 3 | negative |
| 1316 | C755G | S252W | S252W | endometrioid | III | 1 | negative |
| 1792 | C755G | S252W | S252W | endometrioid | III | 1 | positive |
| 1438 | C755G | S252W | S252W | serous | IV | 3 | negative |
| 1482 | C755G | S252W | S252W | endometrioid | IV | 2 | positive |
| 1267 | T1650A | N550K | N549K | endometrioid | II | 2 | positive |
| 1391 | T1650A | N550K | N549K | endometrioid | III | 2 | positive |
| 1528 | T1650G | N550K | N549K | endometrioid | IV | 2 | negative |
| 1655 | A1127G | Y376C | Y375C | endometrioid | III | 2 | positive |
| 1492[d] | A1127G | Y376C | Y375C | endometrioid | I | 1 | negative |
| 1684 | C1118G | S373C | S372C | endometrioid | I | 1 | positive |
| 1094 | T1147C | C383R | C382R | endometrioid | I | 1 | positive |
| 1361 | T1175G | M392R | M391R | endometrioid | I | 1 | positive |
| 1744 | A1642G | I548V | I547V | endometrioid | III | 2 | positive |
| 1717 | A1978G | K660E | K659E | endometrioid | I | 2 | negative |
| 1272 | Intron10 A > C + 2 | | | endometrioid | I | 1 | negative |
| 1289 | 2290-91 del CT | Frameshift | Frameshift | endometrioid | I | 3 | positive |

[a]Numbering relative to NM_022970.2
[b]Numbering relative to P_075259.2
[c]Numbering relative to NP_000132.1
[d]Two mutations in one sample.
[e]Numbering according the NM_000141 as ESS-1 was derived from a stromal sarcoma expressing the FGFR2c isoform.
[f]There is not an alanine at the equivalent position in FGFR2b.

For all mutations, constitutional DNA was sequenced to confirm that the mutation arose somatically. Among the endometrioid cases, there was an excess of FGFR2 mutations in cases with mismatch repair deficiency (11 of 49, 22%) compared with cases with normal mismatch repair (6 of 61, 10%), although it did not reach statistical significance (p=0.10). It should be noted that microsatellite instability (MSI) status was not determined for five tumors. We did not include the 2 bp deletion in an MSI positive case as it is unlikely to be activating and thus may represent a bystander mutation. Although there is an excess of mutations in tumors demonstrating microsatellite instability, we would argue that these mutations in FGFR2 are pathogenic due to the fact that the same mutations are observed in both MSI positive and microsatellite stable (MSS) primary tumors and that the majority of the mutations are identical to those activating mutations identified in the germline, a coincidence one would not expect if they were bystander mutations associated with microsatellite instability.

Of the 11 different mutations we identified, 7 had previously been reported associated with craniosynostosis or skeletal dysplasia syndromes, one (A315T) occurred at a FGFR2c residue at which a similar missense mutation had been reported (A315S) and four mutations were novel (FIG. 1). The distribution of mutations according to tumor histotype, along with tumor grade and stage harboring FGFR2 cause Apert syndrome, the most severe of the craniosynostosis syndromes characterized by craniosynostosis as well as severe syndactyly of the hands and feet (Park et al., 1995).

A combination of studies utilizing biochemical, structural and biological assays have shown that the S252W mutation demonstrates increased ligand binding and ligand promiscuity (Ibrahimi et al., 2001; Ibrahimi et al., 2004; Yu et al., 2000). Extensive in vitro affinity studies have been performed with both the S252W FGFR2c and S252W FGFR2b mutant receptors showing that this mutation increases the binding affinity of the receptor for multiple FGFs from 2-8 fold, in addition to violating the ligand binding specificities attributed to the alternatively spliced isoforms (Ibrahimi et al., 2004).

The prevalence of the S252W mutation in this panel of tumors suggests positive selection for this mutant in endometrioid endometrial cancers. Although the expression of all FGF ligands has not been examined in normal cycling endometrium and endometrial cancers, there are several studies reporting the expression of FGF2 predominantly in the basal part of luminal and glandular epithelium (Moller et al., 2001; Sangha et al., 1997). Several studies have also shown an increase in FGF2 expression in the glandular epithelia associated with complex hyperplasia and adenocarcinoma (Gold et al., 1994). Endometrial epithelial cells normally express only the FGFR2b isoform which cannot bind FGF2. However, the acquisition of the S252W mutation in these cells would be anticipated to result in autocrine activation of the S252W FGFR2b receptor. The S252W mutation also enables the mutant receptor to bind FGF9 which is highly expressed in the endometrial stroma (Tsai et al., 2002). The prevalence of the S252W mutation suggests that the different FGFR2 isoforms play important roles in mediating directional epithelial-mesenchymal signaling in the endometrium.

Four additional extracellular domain mutations were identified, K310R and A315T in the cell lines and S373C (S372C) and Y376C (Y375C) in primary tumors, the latter mutation seen in two independent tumors (FIG. 1, Table 2). Functional studies performed on those extracellular mutations in FGFR2c (or the paralogous FGFR3) resulting in either the loss or gain of an additional cysteine residue have demonstrated that these missense changes result in constitutive receptor dimerization due to the formation of inter- rather than intra-molecular disulphide bonds (Naski et al., 1996). In the germline, the extracellular juxtamembrane FGFR2c mutations S372C and Y375C have been reported in several individuals with Beare-Stevenson cutis gyrata syndrome, a craniosynostosis syndrome with a broad range of additional clinical features (Przylepa et al., 1996). The paralogous mutations in FGFR3c (G370C and Y373C) are also associated with a severe chondrohyperplasia, thanatophoric dysplasia type I (Rousseau et al., 1996). Similar to the A315S mutation, the A315T mutation is likely to confer upon FGFR2c the ability to bind FGF10 illegitimately (Ibrahimi et al., 2004).

We identified two mutations; C383R (C382C) and M392R (M391E) within the transmembrane domain. The C383R mutation we identified is similar to a non conservative missense mutation at the paralogous position in FGFR3 (G380R) that accounts for over 95% of patients with achondroplasia (Shiang et al., 1994). The FGFR3 G380R mutation has been reported to increase receptor half-life and render the receptor resistant to ligand-induced internalization (Monsonego-Ornan et al., 2000). A more recent study showed that whereas wildtype receptor undergoes lysosomal degradation following ligand stimulation, the mutant G380R mutant receptor is recycled back from the lysosomes to the plasma membrane thus augmenting FGF signaling (Cho et al., 2004). The novel M392R mutation is two residues proximal to the well-studied FGFR3 A391E mutation associated with Crouzon syndrome with acanthosis nigricans (Meyers et al., 1995). Biophysical analysis of the A391E mutation demonstrated a change in the dimerization free energy of the FGFR3 transmembrane domain consistent with stabilization of the dimer (Li et al., 2006). Although the C382R mutation in FGFR2c has previously been shown to result in constitutive receptor phosphorylation and transformation of NIH3T3 cells (Li et al., 1997), elucidation of the exact mechanism of receptor activation by these transmembrane FGFR2b mutations remains to be explored.

In addition to the extracellular and transmembrane domain mutations, four different mutations in the FGFR2 kinase domain were identified. While two of these, N550K (N549K) and K660E (K659E), have not been identified as germline mutations in any craniosynostosis syndromes, the similar N549H mutation in FGFR2c has been associated with Crouzon Syndrome (Kan et al., 2002) and identical mutations at the paralogous positions have been seen in FGFR3 associated with hypochondroplasia (N540K) and thanatophoric dysplasia II (K650E) (Naski et al., 1996). Crystal structures of N549H and K650N mutant FGFR2c kinases show that these mutations activate the kinase by loosening a novel autoinhibitory molecular brake at the kinase hinge region (M. Mohammadi, unpublished results).

The pathological consequence of the novel IVS10+2A>C splicing mutation is unknown, however it is tempting to speculate that this would result in increased receptor signaling. There is alternative splicing in the intracellular juxtamembrane region in FGFR1-3 leading to the inclusion or exclusion of two amino acids, valine and threonine (VT) downstream of exon 10. The IVS10+2A>C mutation results in a GCAAGT non-canonical splice donor site and given that the non canonical GC-AG donor/receptor pair is observed 15-30× more frequently in the genome than the GA-AG donor/receptor pair (Burset et al., 2000; Chong et al., 2004) the IVS10+2A>C mutation may result in an increase in the relative proportion of the +VT isoform. The FRS2 adaptor signaling protein that links FGFRs to the MAPK and PI3K pathways binds to a sequence in the juxtamembrane domain of murine FGFR1 that includes the alternatively splicing VT (Burgar et al., 2002). As such, the IVS10+2A>C mutation likely results in a more efficient splice donor site that increases the levels of the +VT transcript, this in turn would result in increased FRS2a mediated signaling.

One endometrial tumor was shown to carry a novel 2 bp deletion 2287-88 CT, leading to a frameshift and change from LTTNE to LTHNQStop with a premature truncation at codon 766, the last codon of exon 18. This 2 bp deletion may result in a truncated FGFR2 receptor that is constitutively activated in a similar manner to the similarly truncated C3 transcript of FGFR2 (Moffa et al., 2004) or alternatively it may simply represent a bystander mutation.

Two endometrial samples were shown to carry two mutations, the AN3 CA MSI positive cell line which carried N550K (N549K) and K310R and the MSI negative tumor 1492 which carried S252W and Y376C (Y375C). The discovery of two presumably dominantly activating mutations in the same tumor was unexpected. It is interesting to note that in each case there is a mutation that is known to result in constitutive ligand-independent receptor activation, along with either the ligand-dependent S252W or the uncharacterized K310R, suggesting additional selective pressure may exist for increased FGFR2 activation in endometrial epithelia.

EXAMPLE 2

Treatment of Endometrial Cancer by Inhibition of FGFR2

Materials and Methods

Sequencing Analysis

Mutation analysis was performed as previously described (8). PCR primer sequences were M13 tailed and sequencing performed in two directions. Primer sequences are available by request from the author.

Cell Culture and Reagents

The human endometrial MFE296 cell line was purchased from the European Collection of Cell Cultures (Salisbury, Wiltshire, UK). The human endometrial cell lines AN3CA, HEC1A, Ishikawa, RL952, and KLE were provided by Dr. Paul Goodfellow (Washington University, St. Louis, Mo.). MFE296 cells were grown in MEM supplemented with 10% fetal bovine serum (FBS), 2 mM L-glutamine, and penicillin-streptomycin. AN3CA cells were cultured in DMEM supplemented with 10% FBS, non-essential amino acids, 2 mM L-glutamine, and penicillin-streptomycin. HEC1A cells were cultured in 50% DMEM and 50% RPMI 1640, supplemented with 10% FBS and penicillin-streptomycin. Ishikawa and RL952 cells were grown in DMEM supplemented with 10% FBS, non-essential amino acids, and penicillin-streptomycin. KLE cells were grown in 50% DMEM and 50% F-12 media supplemented with 10% FBS and penicillin-streptomycin. All media, FBS, and supplements were purchased from Invitrogen (Carlsbad, Calif.). All cells were grown at 37 C in a humidified atmosphere containing 5% $CO_2$. PD173074 was purchased from Sigma-Aldrich (St. Louis, Mo.), reconstituted in DMSO at a stock concentration of 1 mM, and stored at −20 C. The KH1-LV lentivector plasmid was kindly provided by Dr. Maria S. Soengas (University of Michigan, Ann Arbor, Mich.), and the pNHP, pVSV-G, and pTAT lentiviral packaging plasmids were kindly provided by Dr. Matthew Huentelman (Translational Genomics Research Institute, Phoenix, Ariz.).

shRNA Design

Two independent shRNA constructs, targeting two different exons of FGFR2 (exon 2 and exon 15), were designed against the following sequences: shRNA targeting exon 2: TTAGTTGAGGATACCACATTA (SEQ ID NO:4; nucleotides 79-99, NM_022970); shRNA targeting exon 15: ATGTATTCATCGAGATTTA (SEQ ID NO:5; nucleotides 1866-1884, NM_022970). A nonsilencing shRNA construct was also designed based on a nonsilencing siRNA sequence from Qiagen (SEQ ID NO:6; AATTCTCCGAACGTGTCACGT), and was used as a negative control. The corresponding oligonucleotides were annealed and cloned into the KH1-LV lentivector. The KH1-LV self-inactivating lentiviral vector allows expression of short hairpin sequences under the control of the H1 promoter and GFP expression under the control of the human ubiquitin-C promoter, enabling easy monitoring of transduction efficiency. Cloning strategies are available from the authors upon request.

Lentiviral Production

75-$cm^2$ culture flasks were coated with 50 mg/ml poly-D-lysine (Sigma-Aldrich, St. Louis, Mo.) and HEK293FT cells (Invitrogen, Carlsbad, Calif.) seeded at a density of 8×$10^6$ cells per flask. The following day, the cells were transfected with 7.1 μg pNHP, 2.8 μg pVSV-G, 0.5 μg pTAT, and 3.5 μg KH1-LV using SuperFect transfection reagent (Qiagen, Valencia, Calif.) at a 4:1 ratio of SuperFect (μl) to DNA (μg), according to the manufacturer's protocol. Media containing the virus was collected 24 and 40 hours later, combined, filtered through a 0.45-mm low-protein-binding Durapore® filter (Millipore Corporation, Billerica, Mass.) to remove cell debris, and the viral preparation aliquoted and stored at −80° C. until use.

Lentiviral Transduction

Cells were plated at a density of 4×$10^5$ cells per well in a 6 well plate. The next day, cells were infected with lentiviral stocks in the presence of 6 μg/ml polybrene (Sigma-Aldrich, St. Louis, Mo.). Empty vector and nonsilencing shRNA infections were used as controls for each experiment. Greater than 90% transduction efficiency was achieved in each shRNA experiment, as determined by eGFP visualization (data not shown).

Growth Inhibition Assay

Twenty-four hours after infection, cells were trypsinized and plated in 96 well plates in full growth medium at a density of 5,000 cells per well, in triplicate, and proliferation assessed using the Sulforhodamine B (SRB) assay (Sigma-Aldrich, St. Louis, Mo.). At the indicated time points, wells were fixed with 10% (wt/vol) trichloroacetic acid, stained with SRB for 30 min, and washed with 1% (vol/vol) acetic acid. The protein-bound dye was dissolved in 10 mM Tris base solution, and absorbance measured at 510 nm. For PD173074 drug studies, cells were plated in full growth medium at a density of 5,000 cells per well in a 96 well plate. The next day, increasing concentrations of PD173074 were added and proliferation assessed 72 hours later using the SRB assay.

Annexin V-FITC Labeling of Apoptotic Cells

Annexin V-FITC staining was used to measure phosphatidylserine exposure on cells undergoing apoptosis, according to the manufacturer's instructions (BioVision, Inc. Mountain View, Calif.). Knockdown was achieved with siRNAs rather than the shRNA constructs as the latter also expressed GFP, which has an overlapping emission spectra with FITC. 2.5×$10^5$ cells were plated per well in a 6 well plate. Twenty-four hours later, cells were transfected with 25 nM nonsilencing (NS) siRNA or FGFR2 siRNA X2 using Lipofectamine 2000 transfection reagent. The siRNA duplex was allowed to form a complex with Lipofectamine 2000 for 20 minutes at room temperature, and transfection carried out at 37° C. for 24 hours. 48 hours after transfection, floating and attached cells were collected, washed in cold PBS, resuspended in Annexin binding buffer (10 mM Hepes (pH 7.4), 140 mM NaCl, 2.5 mM $CaCl2$), stained with 500 ng/mL annexinV-FITC and 1 μg/mL propidium iodide (Sigma-Aldrich, St. Louis, Mo.), and analyzed for annexin positive cells using a CyAn ADP flow cytometer and Summit software, version 4.3 (Dako Cytomation, Carpinteria, Calif.). For PD173074 studies, cells were plated at a density of 1×$10^5$ cells per well in a 6 well plate. 24 hours later, cells were treated with 1 μM PD173074 or DMSO (vehicle control), and, at the indicated time point, stained with AnnexinV-FITC and analyzed by flow cytometry.

Cell Cycle Analysis

Cells were plated at a density of 1×$10^5$ cells per well in a 6 well plate. The next day, cells were treated with 1 μM PD173074 or DMSO (vehicle control). 72 hours later, cells were stained with propidium iodide as described {Krishan, 1975 #28} and analyzed by flow cytometry. Cell cycle analysis was performed using ModFit software (Verity Software House, Inc. Topsham, Me.).

Western Blot Analysis

Cells were plated in 60 $mm^2$ dishes at a density of 2×$10^6$ cells per dish. The next day cells were starved overnight for 18 hours in 0.2% FBS or maintained in full growth media, and then incubated with increasing concentrations of PD173074 for three hours. Cells were washed in ice cold PBS, lysed in kinase buffer [20 mM Hepes pH7.4, 2 mM EGTA, 1% Triton X100, 10% glycerol, 1 mM $Na_3VO_4$, 1 mM NaF, 100 uM AEBSF, and 1 tablet/10 mL of Mini Complete Protease Inhibitor (Roche Molecular Biochemicals, Indianapolis, Ind.)], briefly sonicated on ice, and protein concentrations estimated using Quick Start Bradford Reagent with bovine gamma-globulin standards (Bio-Rad Laboratories, Hercules, Calif.). Equal amounts of protein were separated by SDS-PAGE on 4-12% gradient gels and transferred to polyvinylidene difluoride membranes (Invitrogen, Carlsbad, Calif.). Membranes were immunoblotted with antibodies to phosphorylated and total AKT, ERK1/2, p38, STAT-3 and STAT-5, PLCγ and total PTEN (Cell Signaling Technology, Beverly, Mass.). FGFR2 expression was detected with BekC17 antibody (Santa Cruz Biotechnology, Inc., Santa Cruz, Calif.). Horseradish peroxidase-conjugated goat anti-mouse or anti-rabbit secondary antibodies (Biomeda, Foster City, Calif.), were used, followed by chemiluminescence staining. For shRNA studies, lysates were collected 48 hours after shRNA transduction and processed as described above.

Statistical Analysis

Statistical analyses were performed using GraphPad Prism version 4.0 for Macintosh (GraphPad Software, San Diego, Calif.). IC50 values were calculated by dose-response analysis using nonlinear regression of sigmoidal dose response with variable slope. Apoptosis data were analyzed by one-way ANOVA. Significant differences between treatment groups were determined using a Student's t test. All P values were considered significant when $P<0.05$. Data were expressed as mean±SE.

Results

Patterns of FGFR2, PTEN and KRAS2 mutations in primary endometrial cancers: concomitant FGFR2 and PTEN mutation and mutually exclusive FGFR2 and KRAS2 mutation.

116) of tumors. Of those tumors with FGFR2 mutations, 77% (14/18) also carried a PTEN mutation, demonstrating that mutations in FGFR2 frequently occur alongside PTEN mutations in endometrioid endometrial tumors. KRAS mutations were identified in 12% (15/116) of tumors. Activating mutations in GFR2 and KRAS were mutually exclusive. Of note, one tumor possessed a frameshift mutation in FGFR2 (2290-91 del CT) and contained a KRAS mutation. However, as the pathogenic nature of this FGFR2 mutation is unknown, we concluded that activating mutations in FGFR2 were mutually exclusive with activating mutations in KRAS. PTEN inactivating mutations occurred alongside both KRAS and FGFR2 mutations (Table 3).

| Case ID | FGFR2 Mutation | KRAS Mutation | PTEN Mutation | Stage | Grade | MSI |
|---|---|---|---|---|---|---|
| AN3CA | pLys310Arg; Asn550Lys | wt | p. Arg130fsX4 | | | + |
| MFE296 | p. Asn550Lys | wt | wt | | | − |
| 1359 | p. Ser252Trp | wt | wt | I | 2 | + |
| 1574 | p. Ser252Trp | wt | p. [Gly44AlafsX7 (+) Y68X] | I | 2 | + |
| 1492 | p. Ser252Trp; Tyr376Cys | wt | p. Arg130Gly | I | 1 | − |
| 1484 | p. Ser252Trp | wt | p. [Arg130Gly (+) F56V] | III | 3 | − |
| 1316 | p. Ser252Trp | wt | p. Leu112Val | III | 1 | − |
| 1792 | p. Ser252Trp | wt | wt | III | 1 | + |
| 1482 | p. Ser252Trp | wt | p. Thr319X | IV | 2 | + |
| 1267 | p. Asn550Lys | wt | p. AlaA126Asp | II | 2 | + |
| 1391 | p. Asn550Lys | wt | p. Q245X | III | 2 | + |
| 1528 | p. Asn550Lys | wt | p. Arg130Gly | IV | 2 | − |
| 1655 | p. Tyr376Cys | wt | p. Arg308IlefsX5 | III | 2 | + |
| 1684 | p. Ser373Cys | wt | p. Arg130Gly | I | 1 | + |
| 1094 | p. Cys383Arg | wt | p. Leu108-Asp109 | I | 1 | + |
| 1361 | p. Met392Arg | wt | p. Thr319X | I | 1 | + |
| 1744 | p. Ile548Val | wt | p. [Phe21SerfsX2 (+) K66N] | III | 2 | + |
| 1717 | p. Lys660Glu | wt | p. Ser59X | I | 2 | − |
| 1272 | c. 1287 + 2A > C | wt | wt | I | 1 | − |
| 1289 | p. Thr762fsX3 | wt | wt | I | 3 | + |
| 1284 | wt | p. Gly12Asp | p. [Arg130Gly (+) Gly165Arg] | II | 1 | + |
| 1606 | wt | p. Gly12Asp | p. Val191GlyfsX7 | I | 1 | − |
| 1856 | wt | p. Gly12Asp | wt | I | 2 | + |
| 1411 | wt | p. Gly12Ala | p. [Arg47Gly (+) Gly165Arg] | III | 2 | + |
| 1966 | wt | p. Gly12Ala | p. [Arg130X (+) Ala148LysfsX3] | III | 2 | + |
| 1393 | wt | p. Gly12Cys | p. Ile4HisfsX5 | III | 2 | + |
| 1609 | wt | p. Gly12Cys | p. Lys267ArgfsX8 | I | 3 | + |
| 1044 | wt | p. Gly12Val | p. Arg130Gln | III | 3 | + |
| 1599 | wt | p. Gly12Val | p. [Arg130Gly (+) Gln171X] | III | 2 | + |
| 1873 | wt | p. Gly12Val | p. V290X | I | 1 | + |
| 1656 | wt | p. Gly12Val | p. Gly251ValfsX5 | I | I | − |
| 1664 | wt | p. Gly12Asp | p. Tyr16LeufsX27 | III | 1 | − |
| 1287 | wt | p. Gly13Asp | p. [H123Y (+) Ala126Ser] | III | 1 | − |
| 1576 | wt | p. Gly13Asp | p. Arg130Gln | I | 2 | + |

Numbering relative to FGFR2 protein sequence NP_075259.2; KRAS protein sequence NP_203524.1; PTEN protein sequence NP_000305.3.

Figure 1A:
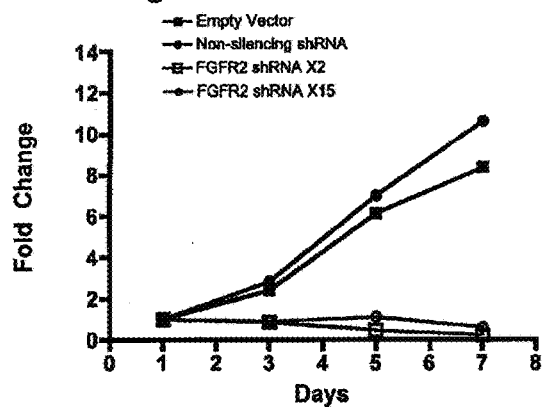
FIGS. 1A-E show the results of a shRNA mediated knockdown of FGFR2 in ANC3A and MFE296 cells, resulting in cell death of the endometrial cells.
Figure 1B:
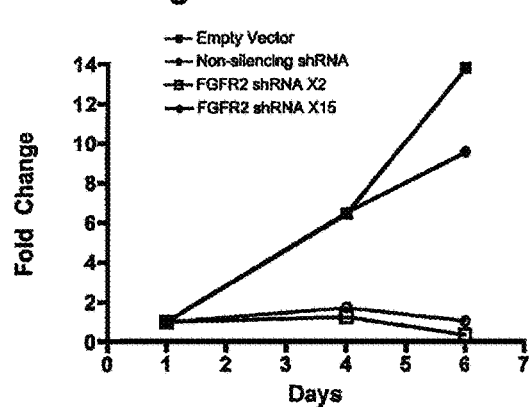
Figure 1C:
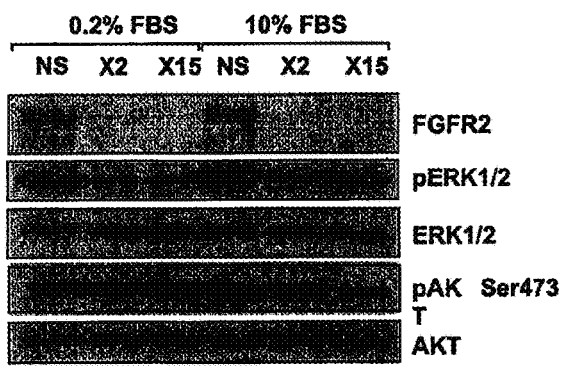
Figure 1D:
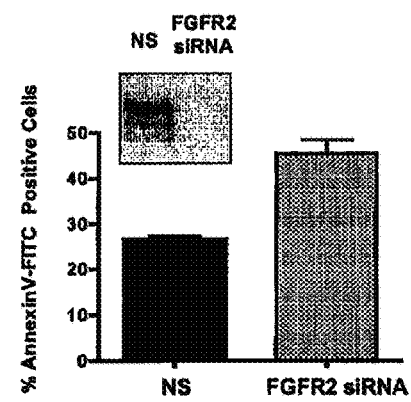
Figure 1E:

Given that PTEN and KRAS2 mutations are common in endometrioid endometrial cancer, we first sought to determine whether FGFR2 activation occurred in tumors that harbor loss-of-function mutations in PTEN and/or gain-of-function mutations in KRAS. We sequenced all nine exons of PTEN and exon one of KRAS in 116 endometrial tumors for which we knew the FGFR2 mutation status. Due to the limiting amount of DNA available, we only sequenced exon one of KRAS, as mutations in exon one account for greater than 96% of KRAS mutations in endometrioid endometrial cancer (The Catalog of Somatic Mutations in Cancer). Mutation analysis revealed PTEN mutations in 70% (82/ shRNA Knockdown of FGFR2 Induces Cell Death in Endometrial Cancer Cells, Despite PTEN Inactivation Given the occurrence of activating FGFR2 mutations within the context of PTEN inactivation in endometrial cancer and the known role of the PI3K/AKT pathway in promoting cell survival, we next sought to determine whether inhibition of FGFR2 could induce cell death in the presence of PTEN inactivation. The impact of shRNA knockdown of FGFR2 expression on cell proliferation was assessed in AN3CA and MFE296 endometrial cancer cells, both of which carry an activating FGFR2 mutation. In addition, AN3CA has mutations in both PTEN alleles and does not express PTEN (FIG. 1E). In addition, AN3CA has mutations in both PTEN alleles and does not express PTEN. MFE296, on the other hand, is wildtype for PTEN and PIK3CA (The Catalog of Somatic Mutations in Cancer). AN3CA and MFE296 cells were lentivirally transduced with two independent shRNAs targeting FGFR2. Cell proliferation and viability were measured at multiple time points. Knockdown of FGFR2 inhibited cell proliferation in both AN3CA and MFE296 cells (FIG. 1A, B), demonstrating the effectiveness of targeting activated FGFR2 even in the presence of PTEN inactivation. Knockdown of FGFR2 expression was confirmed and phosphorylation of ERK1/2 and AKT was examined by Western blot 48 hours after shRNA transduction. As shown in FIG. 1C, both FGFR2 shRNA constructs resulted in greater than 90% knockdown of FGFR2 protein. A decrease in the levels of phospho-ERK1/2 was seen in AN3CA cells following FGFR2 knockdown. The effect was more prominent when the cells were grown in 0.2% FBS. However, no change in AKT phosphorylation at Serine 473 was observed (FIG. 1C), consistent with the PTEN mutation status of this cell line.

To confirm that the cell death observed following FGFR2 knockdown was due to induction of apoptosis, AN3CA cells were transfected with siRNA targeted towards FGFR2 and labeled with Annexin V-FITC to detect exposed phosphatidylserine by flow cytometry. An increase in Annexin V-FITC positive staining was evident 48 hours following transfection with FGFR2 siRNA compared to the nonsilencing siRNA control, indicating that these cells were undergoing apoptosis (FIG. 1D). The dramatic inhibition of cell viability observed following knockdown of FGFR2 suggests that these cells may demonstrate oncogene addiction. Activated FGFR2 is therefore a potential therapeutic target in endometrial cancer.

Figure 2A:
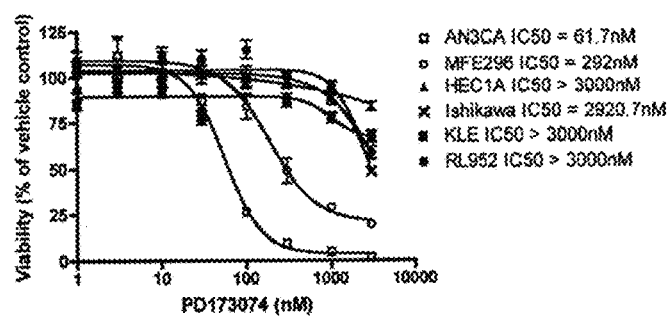
FIGS. 2A-C. Endometrial cancer cells expressing activated FGFR2 are sensitive to PD173074, a pan-FGFR inhibitor. Dose response curves for six endometrial cancer cell lines. Cell viability was measured with the SRB assay 72 hours following addition of PD173074. AN3CA and MFE296 cells carry the N550K FGFR2 mutation. HEC1A, Ishikawa, KLE, and RL952 are wildtype for FGFR2. PD173074 had a profound negative effect on cell viability of cell lines expressing mutant FGFR2 compared to those expressing wildtype FGFR2. PD173074 IC50 values: AN3CA=61.7 nM; MFE296=284.3 nM; HEC1A>3000 nM; Ishikawa=2920.7 nM; KLE>1000 nM; RL952>1000 nM.
Figure 2B:
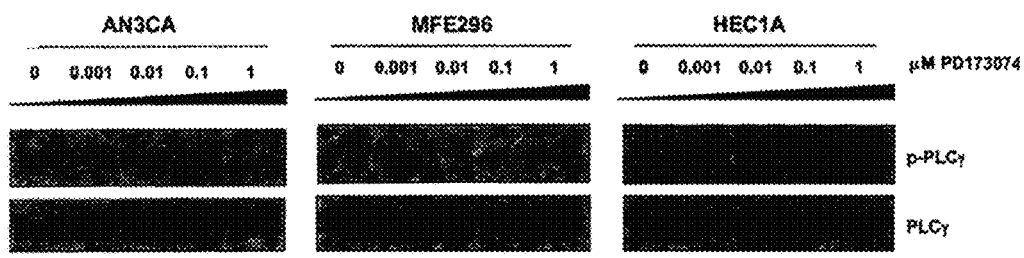
Figure 2C:
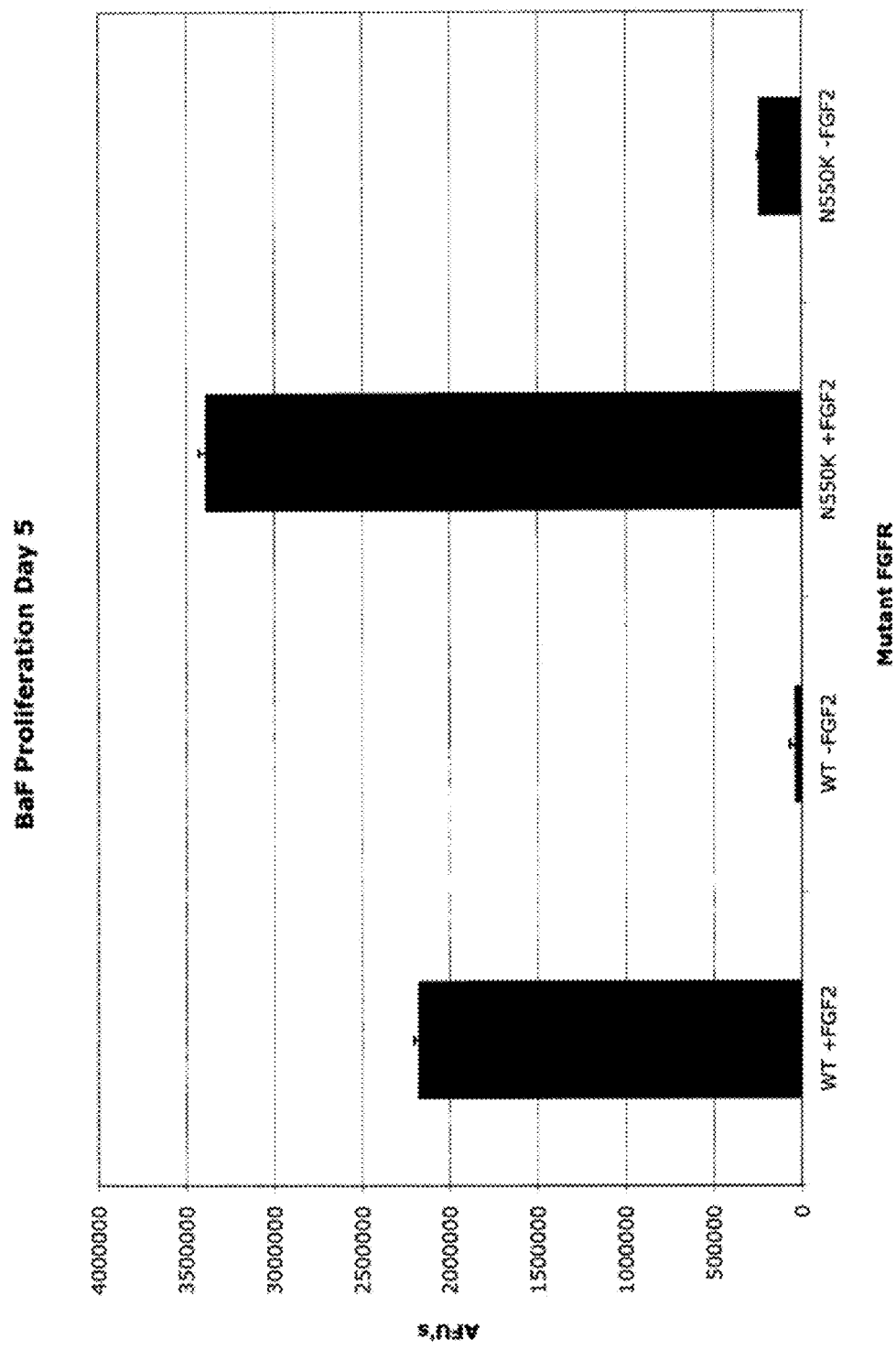
Figure 3A:
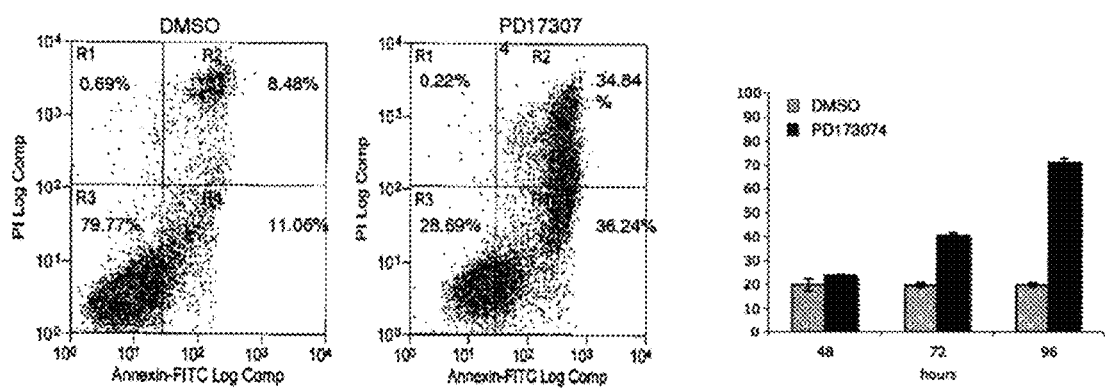
FIGS. 3A-B. FGFR2 inhibition via PD173074 induces cell death and cell cycle arrest in endometrial cancer cells with activated FGFR2.
Figure 3B:
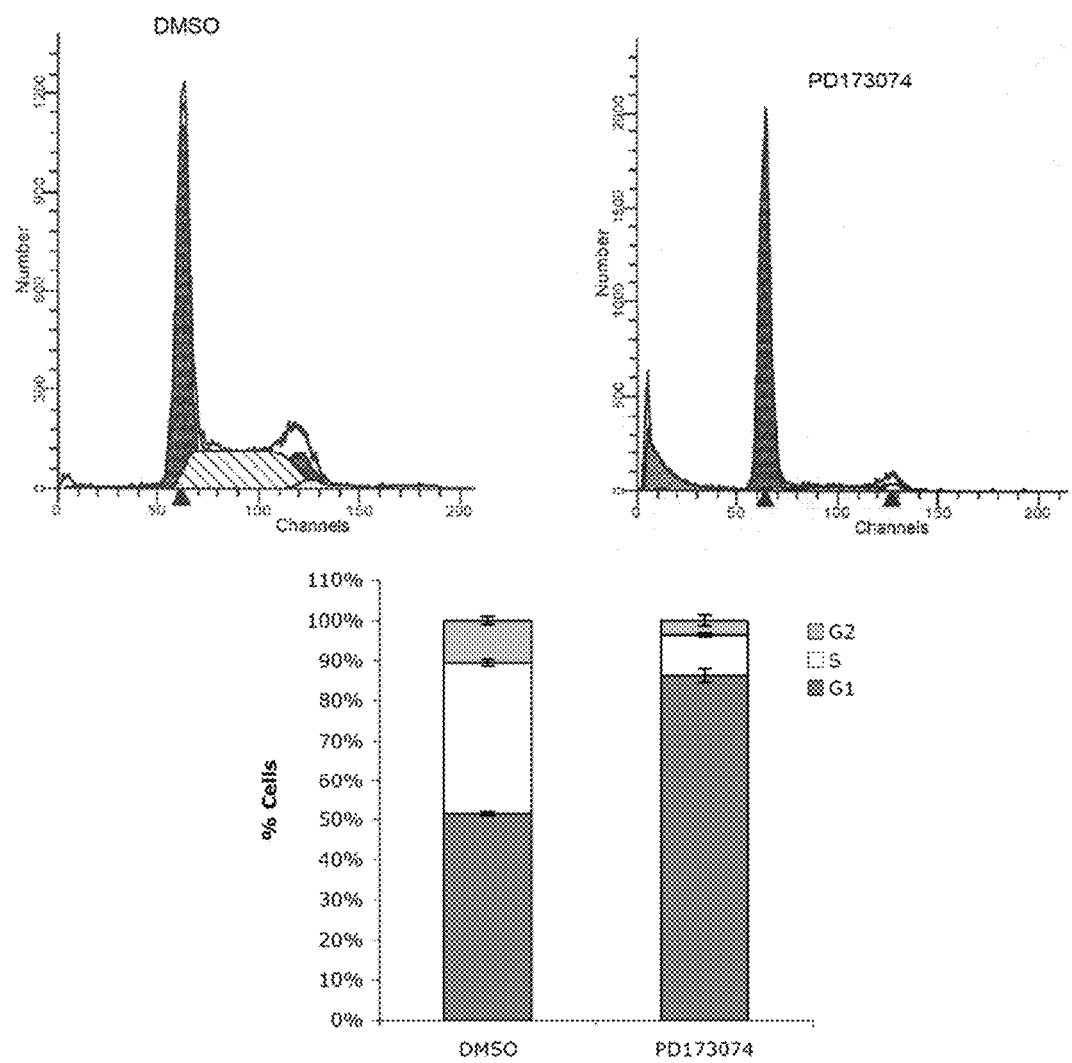

Endometrial Cancer Cells Expressing Activated FGFR2 are Sensitive to PD173074, a Pan-FGFR Inhibitor Six endometrial cancer cell lines (2 mutant N550K FGFR2, and 4 wildtype FGFR2) were treated with increasing concentrations of PD173074, a pan-FGFR tyrosine kinase inhibitor. This inhibitor demonstrates high selectivity against FGFRs (FGFR1, IC50=~25 nM) and VEGFs (VEGFR2, IC50=~100 nM) and has been shown to induce apoptosis in myeloma cells with an activating t(4; 14) translocation and activating mutations in FGFR3 (10). As shown in FIG. 2A, the two endometrial cancer cell lines with mutant FGFR2 were 10-40× more sensitive to inhibition with PD173074 than cell lines with wild type FGFR2. The AN3CA line, which has loss-of-function mutations on both PTEN alleles, was the most sensitive cell line. Annexin V-FITC labeling indicated that ~70% of AN3CA cells were undergoing apoptosis 96 hours after drug treatment (FIG. 3A). In addition, cell cycle analysis revealed PD173074 treatment induced G1 arrest of AN3CA cells (FIG. 3B). As shown in FIG. 2C, the constitutively active FGFR2 kinase domain mutation N550K results in an increase in proliferation over that induced by the wild type receptor (WT) both in the absence (−FGF2) of and in the presence (+FGF2) of exogenous FGF2 ligand. These data suggest that whilst the N550K mutation is constitutively active, it also requires ligand for full activity. The murine interleukin-dependent pro-B BaF3 cell line is routinely used as a model system for the evaluation of receptor tyrosine kinase function. Although BaF3 cell proliferation and survival is normally dependent on IL-3, activated receptor tyrosine kinase signaling can substitute for IL-3 to maintain cell viability and proliferation. Proliferation assays are performed in the absence of IL-3 and in the presence of 1 nM FGF2 and 10 ug/ml heparin and proliferation assayed after 5 days using the ViaLight Plus Cell Proliferation/Cytotoxicity Kit (Lonza Rockland Inc) according to manufacturers instructions.

Cell Death Following Pan-FGFR Inhibition is Associated with Inhibition of ERK, Partial Inhibition of AKT, but not Inhibition STAT3 or Activation of p38

Figure 4:
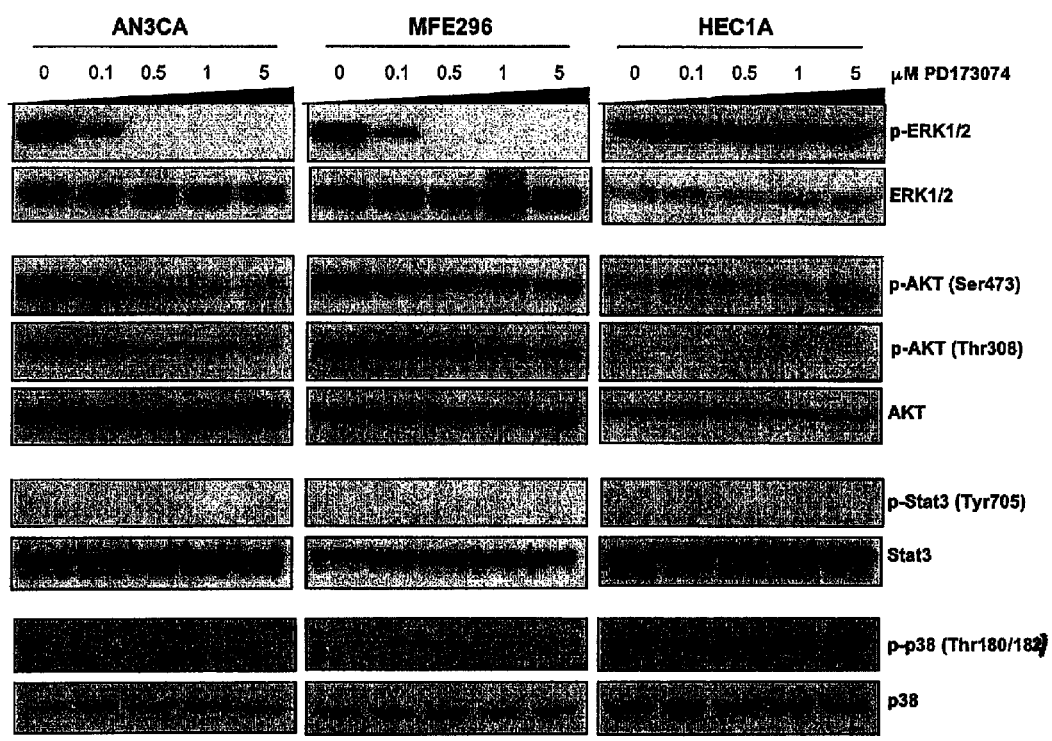
FIG. 4. Activation status of key signaling molecules following treatment with increasing concentrations of PD173074. Cells were treated with increasing concentrations of PD173074 in 10% FBS for 3 hours. Lysates were collected and evaluated by Western blot analysis for activation of ERK1/2, AKT, STAT3, and p38. PD173074 treatment resulted in suppression of ERK1/2 activation, modest suppression of AKT phosphorylation, but had no effect on STAT3 or p38 activation in AN3CA and MFE296 cells. PD173074 had no effect on ERK1/2, AKT, STAT3, or p38 activation in HEC1A cells.

Inhibition of phosphorylation of ERK1/2, AKT, and STAT3/5, coupled with delayed activation of p38, has been reported to be a common feature associated with the induction of cell death in cells demonstrating oncogene addiction (17). To determine whether PD173074 treatment resulted in a similar inhibition of these pathways, ERK1/2, AKT, STAT3/5, and p38 phosphorylation levels were evaluated by Western blot in three cell lines (two sensitive and one resistant to PD173074). STAT5 expression was not detectable by Western blot in these three cell lines (data not shown). As shown in FIG. 4, treatment with PD173074 for three hours resulted in a concentration dependent decrease in ERK1/2 phosphorylation in AN3CA and MFE296 cells. HEC1A cells, which express wildtype FGFR2 and are resistant to PD173074, did not show a decrease in ERK1/2 phosphorylation. This is consistent with downstream activation of the MAPK pathway in this cell line, due to a KRAS2 G12D mutation (The Catalog of Somatic Mutations in Cancer).

PD173074 treatment also resulted in a moderate reduction in phosphorylation of AKT at Threonine 308 and Serine 473 in AN3CA and MFE296 cells. No decrease in activation of AKT was evident in HEC1A cells. Notably, PD173074 treatment had no effect on STAT3 or p38 phosphorylation in any of the cell lines tested (FIG. 4). We also examined activation of PLCγ, as FGFRs have been shown to signal through this pathway (18); no change in PLCγ activation was observed following PD173074 treatment (data not shown).

Though no change in STAT3 or p38 activation was evident three hours following PD173074 treatment, previous models of oncogene addiction have shown that activation of p38 is delayed, peaking at 8-24 hours following oncogene inhibition {Sharma, 2006 #17}. Therefore, we evaluated ERK1/2, AKT, STAT3, and p38 activation at various time points ranging from 0 to 72 hours following PD173074 treatment. Consistent with data presented in FIG. 4, PD173074 treatment resulted in a rapid reduction in ERK1/2 activation in MFE296 and AN3CA cells, but not HEC1A cells (FIG. 5A). Phosphorylated ERK1/2 began to return 24-48 hours after PD173074 treatment, but had not reached baseline activation by 72 hours. A reduction in phosphorylated AKT was also detected in MFE296 and AN3CA cells, and was more evident at the Threonine 308 site than at Serine 473 (FIG. 5A). The decrease in AKT activation was delayed compared to the rapid inhibition of MAPK phosphorylation, with the greatest decrease in AKT phosphorylation detected at 8 and 24 hours following PD173074 treatment.

Notably, no change in STAT3 or p38 activation was detected in AN3CA and MFE296 cells throughout the time course (FIG. 5A). When the cells were grown in 0.2% FBS media, treatment with PD173074 resulted in a reduction in MAPK activation in both AN3CA and MFE296 (FIG. 5B), similar to that observed in full growth media. Interestingly, PD173074 treatment in 0.2% FBS media resulted in a modest reduction in phospho-AKT at Threonine 308 and a slight reduction at Serine 473 in AN3CA and MFE296 cells. The constitutive activation of AKT in the AN3CA cell line in 0.2% FBS is likely due to inactivation of both PTEN alleles; the mechanism of constitutive AKT activation is unknown in MFE296 cells as they express wildtype PTEN and PIK3CA.

Discussion

Understanding the molecular basis of tumor progression has led to the development and success of targeted therapies in variety of cancer types ({Pickering, 2008 #27}. There is increasing evidence that activating mutations in genes involved in various signaling pathways can result in "addiction" of tumor cells to these pathways {Sharma, 2007 #31}. Furthermore, these activating mutations serve not only to identify potential therapeutic targets but their presence can also predict clinical response to pathway inhibition {Lynch, 2004 #30}. However, it has become increasingly clear that the response to target inhibition is influenced by the molecular context wherein these mutations occur. As we have previously identified activating mutations in FGFR2 in ~16% of endometrioid endometrial tumors, here we sought to investigate the genetic context in which FGFR2 mutations occur in endometrial cancer. We also sought to evaluate the therapeutic potential of targeting activated FGFR2 by investigating the biological consequence of inhibiting FGFR2 in endometrial cancer cells possessing activating mutations in FGFR2.

In the present study, we evaluated the KRAS and PTEN mutation status of endometrioid endometrial tumors with known FGFR2 mutation status. Activating KRAS and FGFR2 mutations did not occur together in the same tumor, consistent with FGFR2 driving tumorigenesis through the MAPK pathway. FGFR2 activation occurred alongside PTEN inactivation, suggesting that, at least in endometrial cells, FGFR2 does not mediate its biological effect through PI3K/AKT. This is supported by one previous report where FGF7 or FGF10 stimulation of endometrial cells resulted in ERK1/2, but not AKT, activation (19). PTEN and KRAS mutations occurred within the same tumor, consistent with a previous report (20).

We have also shown that FGFR2 signaling is essential for survival and proliferation of AN3CA and MFE296 endometrial cancer cell lines, which is highly suggestive of oncogene addiction. This is supported by the PD173074 $IC_{50}$ studies in which we demonstrated the two cell lines with activated FGFR2 were selectively sensitive to the pan-FGFR inhibitor, PD173074. It is noteworthy that the AN3CA cells were the most sensitive to PD173074 and are mutant for PTEN. This is of particular importance given the high incidence of PTEN mutations in endometrioid endometrial cancer. It has been suggested that PTEN inactivation may transfer the cell's "oncogene addiction" from an activated receptor pathway to constitutively activated PI3K-AKT signaling, and thus lead to resistance to receptor inhibition (21). Indeed, ErbB2-overexpressing breast tumors with reduced or absent PTEN are relatively resistant to trastuzumab-containing chemotherapy regimens (22, 23). Of note, despite the loss of PTEN, inhibition of FGFR2 with a pan-FGFR inhibitor induced cell death and cell cycle arrest in AN3CA cells. The AN3CA cells are thus still addicted to the oncogenic signal of FGFR2. Interestingly, PD173074 treatment induced cell cycle arrest but did not result in enhanced Annexin V staining in MFE296 cells (data not shown). It remains to be determined whether cell cycle arrest alone is responsible for the efficacy of PD173074 in MFE296 cells, or whether induction of Annexin V negative cell death through an unknown mechanism is also involved.

It has been suggested that oncogene addiction resulting from Src, BCR-ABL and EGFR activation share a common signaling cascade, as oncogene inactivation is associated with a rapid loss of phosphorylated ERK, AKT and STAT3/5 and delayed activation of p38 (17). We report here that inhibition of FGFR2 in full growth media is associated with a loss in phosphorylated ERK and partial inhibition of AKT, but has no effect on the phosphorylation status STAT3 or p38. The mechanism underlying addiction to activated FGFR2 in AN3CA and MFE296 cells is therefore distinct from other models of oncogene addiction.

The cell death induced by pan-FGFR inhibition with PD173074 correlated with complete inhibition of ERK1/2 activation in media supplemented with both 10% FBS and 0.2% FBS. Unexpectedly, given the mutant PTEN status in AN3CA cells, PD173074 treatment resulted in a partial loss of AKT phosphorylation in 10% FBS containing media. It is therefore possible that FGFR2 mediates AKT phosphorylation downstream of PTEN. Indeed, in mouse keratinocytes, insulin-like growth factor-I has been shown to alter AKT phosphorylation through a PI3K-independent mechanism involving protein kinase C-mediated protein phosphatase regulation (24). The mechanism responsible for the decreased AKT phosphorylation observed following PD173074 treatment of AN3CA and MFE296 cells remains to be determined. However, the PD173074 induced cell death observed in AN3CA cells is likely independent of this dephosphorylation of AKT. Concentration-response curves performed in 0.2% FBS generated a similar $IC_{50}$ for AN3CA cells to those generated in 10% FBS (data not shown). As AN3CA cells grown in 0.2% FBS did not exhibit pronounced dephosphorylation of AKT, together these data suggest that dephosphorylation of AKT is not required for PD173074 induced cell death in this cell line.

In summary, we have shown that FGFR2 mutations are coincident with PTEN inactivation and mutually exclusive with KRAS2 mutations in primary endometrioid endometrial cancers.

Blockade of FGFR2 signaling by shRNA knockdown or treatment with a pan-FGFR inhibitor, PD173074, resulted in cell cycle arrest and cell death of endometrial cancer cell lines expressing activated FGFR2. The cellular pathways altered following inhibition of FGFR2, however, were distinct from those observed following inhibition of other oncogenes for which oncogene addiction has been demonstrated. A novel mechanism of oncogene addiction associated with FGFR2 activation in endometrial cancer appears likely. Together these data shows inhibition of constitutively active mutant FGFR2 is therapeutically beneficial for endometrial cancer patients despite the frequent inactivation of PTEN in this cancer type.

EXAMPLE 3

Activating-FGFR2 Mutations Promote Endometrial Cell Migration

Materials and Methods

To determine the ability of FGFR2 mutations to alter the phenotype of primary endometrial epithelial cells, HPV/TERT immortalized primary human endometrial epithelial cells were transduced with wild type FGFR2b or mutant FGFR2b (N550K) and FGF-stimulated migration evaluated.

Briefly, 3×10⁵ cells were seeded on top of 8 μm pore size polycarbonate membranes (Cell Biolabs, Inc) in full growth media containing 1 nM FGF10. 24 hours later, the media was aspirated from inside the insert and non-migratory cells were removed from the top of the insert using cotton-tipped swabs. Migratory cells (those that had passed through the membrane) were stained and the membranes were photographed (5 random fields per insert). The stained cells on the inserts were then solubilized and quantified by measuring absorbance at 570 nm.

Results

Figure 7A:
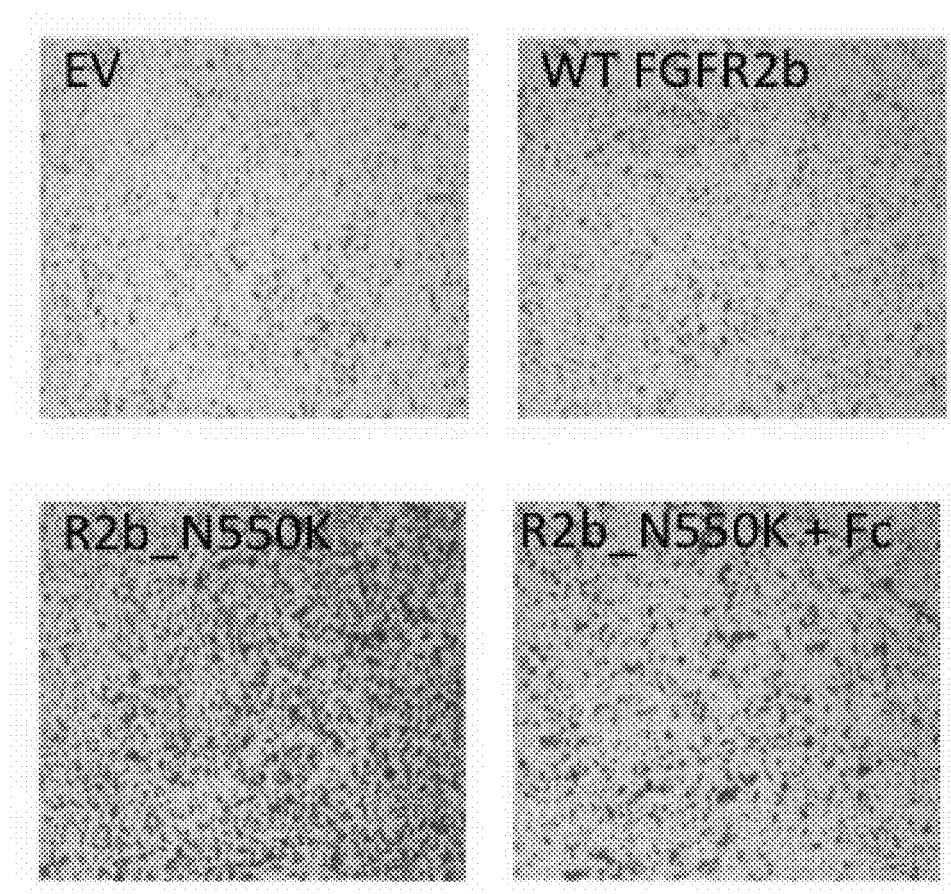
FIGS. 7A-B. Activating-FGFR2 mutations promote endometrial cell migration. Representative images of stained migratory cells transduced with empty vector (EV), wild type FGFR2b (WT FGFR2b), mutant FGFR2b without soluble ligand-trap antibody against FGF10 (R2b_N550K), and mutant FGFR2b with soluble ligand-trap antibody against FGF10 (R2b_N550K+Fc) are shown (FIG. 7A). Absorbance at 570 nm was quantified for each of these groups of stained migratory cells (FIG. 7B), and Western blot analysis was performed to confirm expression of the wild type and mutant FGFR2b (inset image in FIG. 7B).
Figure 7B:
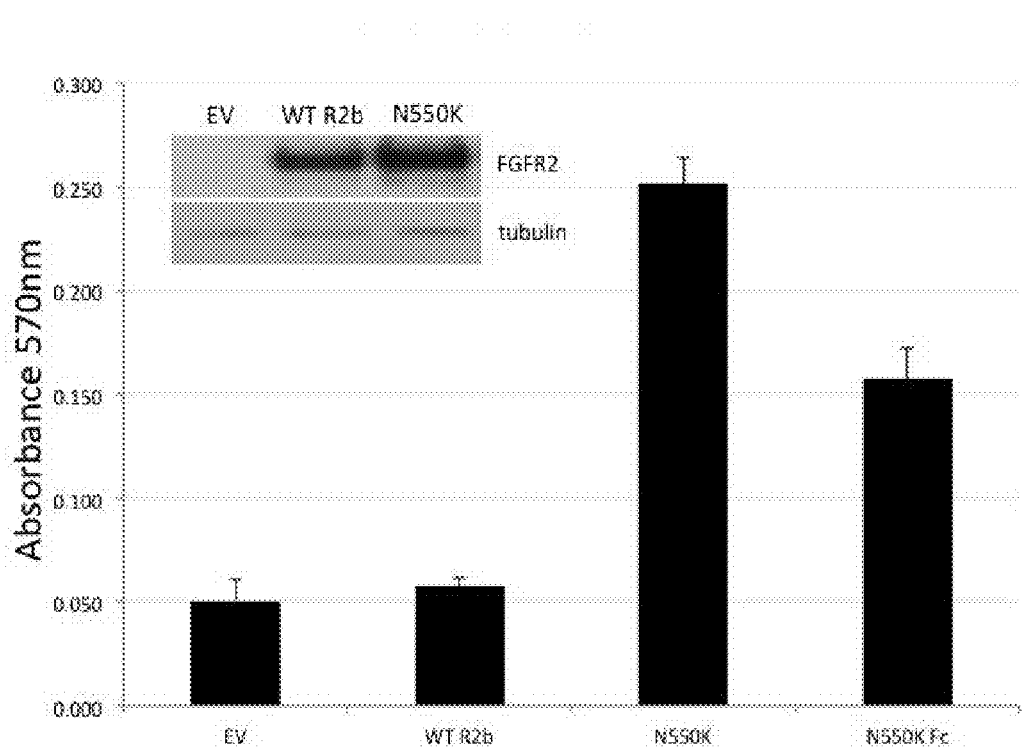

Each FGFR2 construct was assessed in quadruplicate and the results are presented along with representative pictures of the stained cells (see FIG. 7A-B).

The N550K FGFR2b mutation considerably increases the migratory capability of primary endometrial epithelial cells and addition of a soluble ligand-trap antibody against FGF10 markedly inhibits the migration of the N550K mutant cells.

These data indicate that activating-FGFR2b mutations can promote endometrial cell migration and thus support a role for FGFR2 mutations in driving endometrial tumorigenesis and tumor progression.

EXAMPLE 4

Endometrial Tumors with Activating-FGFR2 Mutations are Selectively Sensitive to FGFR Inhibition Materials and Methods To determine the importance of activating-FGFR2 mutations to endometrial tumor growth, xenograft tumors of Hec1A (FGFR2 wt) and AN3CA (FGFR2 N550K mutant) endometrial cancer cells were established and the effect of PD173074, a small molecule FGFR inhibitor, was evaluated.

Briefly, mice were inoculated subcutaneously with 0.1 ml of a 50% RPMI/50% Matrigel™ mixture containing a suspension of tumor cells (1×10⁷ cells/mouse). Once the established tumors reached a mean of approximately 100-150 mg, administration of PD173074 was initiated (25 mg/kg PD173074 twice daily by oral gavage). Tumor weight measurements were recorded three times a week.

Results

Figure 8A:
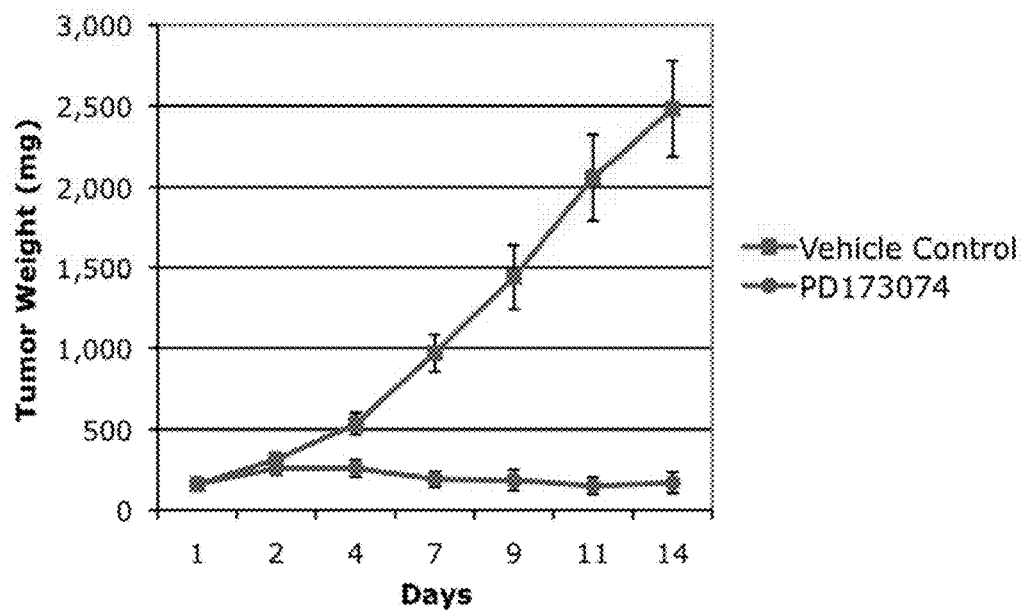
FIGS. 8A-B. Endometrial tumors with activating-FGFR2 mutations are selectively sensitive to FGFR inhibition. Tumor weights were quantified in AN3CA (FGFR2 N550K mutant) xenograft tumors and Hec1A (FGFR2 wild type) xenograft tumors over a period of 14 days and 22 days, respectively. The curves demonstrate that when compared to vehicle control (square symbols) the small molecule inhibitor PD173074 (circle symbols) selectively prevented tumor growth in the AN3CA (FGFR2 N550K mutant) xenograft tumors (FIG. 8A) but not in the Hec1A (FGFR2 wild type) xenograft tumors (FIG. 8B).
Figure 8B:
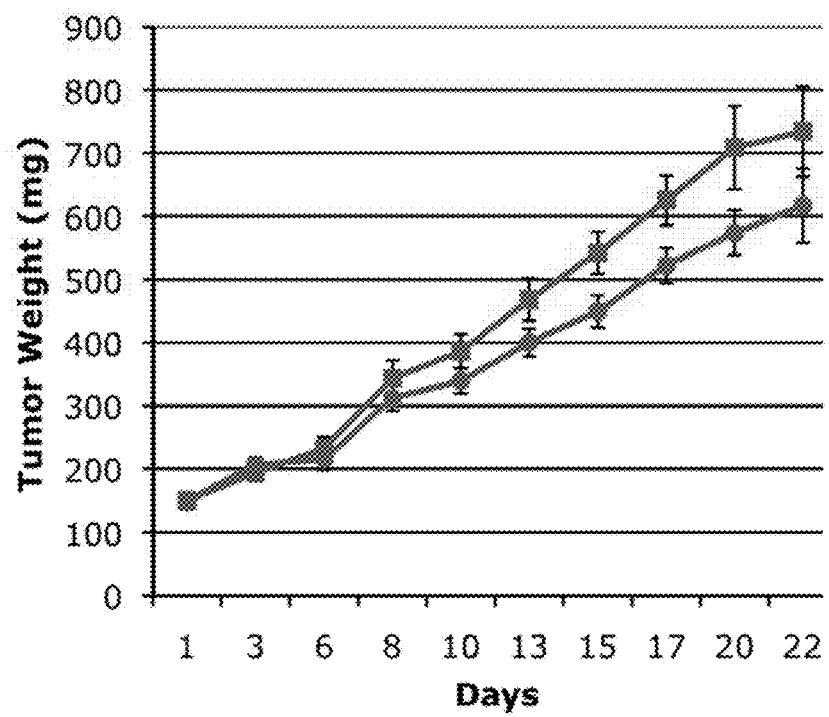

PD173074 treatment suppressed growth of all eight AN3CA xenograft tumors and caused tumor regression of six of the eight AN3CA tumors with a mean tumor shrinkage of 51%. PD173074 treatment had minimal effect on Hec1A (FGFR2 wild type) xenograft tumors (see FIG. 8).

These data demonstrate that endometrial tumors with activating-FGFR2 mutations are selectively sensitive to FGFR inhibition, suggesting that tumors with FGFR2 mutations are "addicted" to the oncogenic FGFR2 signal. Tumors with activating-FGFR2 mutations are dependent on the oncogenic FGFR2 activity.

The present invention is not to be limited in scope by the specific embodiments described herein. Various modification of the invention in addition to those described herein will become apparent to those skilled in the art from the foregoing description and the accompanying figures. Such modifications are intended to fall within the scope of the claims. It is also understood that all values are approximate, and are provided for description purposes only.

All patents, patent application, publications, product descriptions, and protocols cited throughout this application are incorporated herein by reference in their entireties for all purposes.

What is claimed is:

1. A method of treating endometrial cancer characterized by FGFR2 activation in a subject, the method comprising:
   obtaining from the subject a biological sample comprising endometrial cancer cells;
   screening for a FGFR2 activation mutation in the endometrial cancer cells wherein the FGFR2 activation mutation results in an amino acid substitution selected from the group consisting of:
   (a) an S to W mutation at position 252 of SEQ ID NOS:2 (NP_075259.2) or 3 (NP_000132.1);
   (b) a P to R mutation at position 253 of SEC) ID NOS:2 or 3;
   (c) a K to R mutation at position 310 of SEC) ID NOS:2 or 3;
   (d) an A to T mutation at position 315 of SEQ ID NOS:2 or 3;
   (e) an S to C mutation at position 373 of SEQ ID NO:2 or position 372 of SEQ ID NO:3;
   (f) a Y to C mutation at position 376 of SEQ ID NO:2 or position 375 of SEQ ID NO:3;
   (g) a C to R mutation at position 383 of SEQ ID NO:2 or position 382 of SEQ ID NO:3;
   (h) an M to R mutation at position 392 of SEQ ID NO:2 or position 391 of SEQ ID NO:3;
   (i) an I to V mutation at position 548 of SEQ ID NO:2 or position 547 of SEQ ID NO:3;
   (j) an N to K mutation at position 550 of SEQ ID NO:2 or position 549 of SEQ ID NO:3;
   (k) a K to E mutation at position 660 of SEQ ID NO:2 or position 659 of SEQ ID NO:3; and
   (l) a K to N mutation at position 660 of SEQ ID NO:2 or position 659 of SEQ ID NO:3;
   identifying the endometrial cancer cells as susceptible to an FGFR2 inhibitor upon finding the FGFR2 activation mutation in the endometrial cancer cells; and
   administering to the subject with endometrial cancer characterized by FGFR2 activation an effective amount of an FGFR2 inhibitor, wherein the FGFR2 inhibitor is PD173074.

2. The method of claim 1, wherein screening for a FGFR2 activation mutation comprises sequencing DNA from the endometrial cancer cells and/or hybridizing oligonucleotide probes to DNA from the endometrial cancer cells.

3. The method of claim 2, wherein hybridizing oligonucleotide probes to DNA from the endometrial cancer cells occurs on a microarray.

4. The method of claim 3, wherein the oligonucleotide probes specifically hybridize to a site of an FGFR2 activation mutation.

5. The method of claim 1, wherein the endometrial cancer cells are from an endometrioid endometrial tumor.

6. The method of claim 1, wherein the subject is a human having been diagnosed with endometrial cancer.

* * * * *